(12) United States Patent
Decker

(10) Patent No.: US 10,718,454 B2
(45) Date of Patent: Jul. 21, 2020

(54) OXYGEN SUPPLY QUICK CONNECT ADAPTER

(71) Applicant: Specified Medical Technologies, LLC, St. Louis, MO (US)

(72) Inventor: Aaron Decker, Aberdeen, NC (US)

(73) Assignee: Specified Medical Technologies, LLC, St. Louis, MO (US)

( * ) Notice: Subject to any disclaimer, the term of this patent is extended or adjusted under 35 U.S.C. 154(b) by 416 days.

(21) Appl. No.: 15/498,993

(22) Filed: Apr. 27, 2017

(65) Prior Publication Data

US 2017/0241581 A1 Aug. 24, 2017

Related U.S. Application Data

(63) Continuation-in-part of application No. 14/537,158, filed on Nov. 10, 2014, now abandoned.
(Continued)

(51) Int. Cl.
*F16L 37/086* (2006.01)
*F16L 37/35* (2006.01)
(Continued)

(52) U.S. Cl.
CPC ........ *F16L 37/086* (2013.01); *A61M 39/1011* (2013.01); *A61M 39/1055* (2013.01);
(Continued)

(58) Field of Classification Search
CPC .. A61M 16/00; A61M 16/08; A61M 16/0816; A61M 39/00; A61M 39/10; A61M 39/1011; A61M 39/1055; A61M 2039/1016; A61M 2039/1027; A61M 2202/0208; A61M 2205/60; F16L 37/00;
(Continued)

(56) References Cited

U.S. PATENT DOCUMENTS 1,470,209 A 10/1923 White
2,263,293 A 11/1941 Ewald
(Continued)

OTHER PUBLICATIONS

Specified Medical Technologies website, SMT Oxygen Flow Adapter, Aug. 13, 2018, https://smt-medical.net/technology2 (Year: 2018).
(Continued)

*Primary Examiner* — Joseph D. Boecker
(74) *Attorney, Agent, or Firm* — Scott J. Hawranek; Aspire IP

(57) ABSTRACT

Disclosed herein are embodiments of an oxygen quick connect device and method of using the same, the quick connect device includes a female coupling that has a first end and second end and a bore extending longitudinally through the first and second ends and further includes a biased plunger disposed within the bore of the female coupling and configured to reciprocate within, a seal member disposed on the plunger and configured to seal at a location on the bore of the female coupling, a catch device disposed at a second end of the female coupling body, and mechanism for connecting the female coupling to an oxygen supply source. The device also includes a male insert that has a first end and a second end and a first bore extending longitudinally through the first and second ends and groove for engaging with the catch device.

19 Claims, 21 Drawing Sheets

Related U.S. Application Data

(60) Provisional application No. 62/328,229, filed on Apr. 27, 2016.

(51) Int. Cl.
*F16L 37/34* (2006.01)
*A61M 39/10* (2006.01)
*A61M 16/08* (2006.01)

(52) U.S. Cl.
CPC .............. *F16L 37/34* (2013.01); *F16L 37/35* (2013.01); *A61M 16/0816* (2013.01); *A61M 2039/1027* (2013.01); *A61M 2202/0208* (2013.01); *A61M 2205/3334* (2013.01); *A61M 2205/60* (2013.01)

(58) Field of Classification Search
CPC ....... F16L 37/08; F16L 37/084; F16L 37/086; F16L 37/22; F16L 37/28; F16L 37/30; F16L 37/32; F16L 37/34; F16L 37/35; F16L 37/40; F16L 37/413; F16L 37/42
See application file for complete search history.

(56) References Cited

U.S. PATENT DOCUMENTS

| | | | |
|---|---|---|---|
| 2,449,121 A | 9/1948 | Jones | |
| 2,789,654 A | 4/1957 | Zurit | |
| 3,019,646 A | 2/1962 | Gavin | |
| 3,450,424 A | 6/1969 | Calisher | |
| 3,567,175 A | 3/1971 | Sciuto, Jr. | |
| 3,715,099 A | 2/1973 | Shendure | |
| 3,915,386 A | 10/1975 | Vora | |
| D262,739 S | 1/1982 | Nitshke | |
| 4,413,846 A | 11/1983 | Oetiker | |
| 4,436,125 A * | 3/1984 | Blenkush | F16L 37/0841 137/797 |
| 4,541,457 A * | 9/1985 | Blenkush | F16L 37/0841 137/614.05 |
| 4,576,359 A | 3/1986 | Oetiker | |
| 4,582,347 A | 4/1986 | Wilcox et al. | |
| 4,613,112 A * | 9/1986 | Phlipot | F16L 37/22 137/71 |
| 4,641,859 A | 2/1987 | Walters | |
| 4,743,429 A | 5/1988 | Rothenberger | |
| D299,271 S | 1/1989 | Christensen | |
| 4,877,025 A | 10/1989 | Hanson | |
| D313,622 S | 1/1991 | Yazaki | |
| 5,067,750 A | 11/1991 | Minneman | |
| 5,294,092 A | 3/1994 | Wade et al. | |
| 5,489,275 A | 2/1996 | Thompson et al. | |
| 5,540,250 A | 7/1996 | Mullins | |
| 5,569,222 A | 10/1996 | Haselhorst et al. | |
| 5,607,087 A | 3/1997 | Wery et al. | |
| D382,639 S | 8/1997 | Musgrave et al. | |
| 5,695,223 A | 12/1997 | Boticki | |
| 5,702,374 A | 12/1997 | Johnson | |
| 5,816,298 A | 10/1998 | Stricklin et al. | |
| 5,845,943 A * | 12/1998 | Ramacier, Jr. | F16L 37/0841 285/12 |
| 6,010,458 A | 1/2000 | Roberts | |
| 6,279,874 B1 | 8/2001 | Nyberg | |
| 6,354,564 B1 | 3/2002 | Van Scyoc et al. | |
| 6,581,386 B2 | 6/2003 | Young et al. | |
| 6,581,593 B1 | 6/2003 | Rubin et al. | |
| D484,593 S | 12/2003 | Baillargeon et al. | |
| D486,909 S | 2/2004 | Cise et al. | |
| D540,944 S | 4/2007 | Guala | |
| D546,946 S | 7/2007 | Blake et al. | |
| 7,261,125 B1 | 8/2007 | Lien | |
| 7,434,842 B2 | 10/2008 | Schmidt | |
| 7,562,906 B2 | 7/2009 | Schmidt | |
| D605,058 S | 12/2009 | McGrath | |
| D606,972 S | 12/2009 | Schaefer | |
| 7,695,020 B2 | 4/2010 | Schmidt | |
| D657,046 S | 4/2012 | Terry et al. | |
| 8,287,517 B2 | 10/2012 | Hanlon et al. | |
| D671,639 S | 11/2012 | Trifilio | |
| 8,356,794 B1 | 1/2013 | Liu | |
| D678,516 S | 3/2013 | Wong | |
| D679,413 S | 4/2013 | Bucher et al. | |
| 8,470,268 B2 | 6/2013 | Wong | |
| D709,187 S | 7/2014 | Li | |
| D719,650 S | 12/2014 | Arinobe et al. | |
| D727,492 S | 4/2015 | Scampoli | |
| D739,005 S | 9/2015 | Matsumura | |
| D748,783 S | 2/2016 | Zhang et al. | |
| D749,742 S | 2/2016 | Ishibashi et al. | |
| D757,260 S | 5/2016 | Lombardi, III et al. | |
| D760,893 S | 7/2016 | Honda et al. | |
| D773,659 S | 12/2016 | Cain et al. | |
| D775,350 S | 12/2016 | Buess | |
| D788,295 S | 5/2017 | Holmstrom | |
| D805,629 S | 12/2017 | Fiorenza | |
| 2002/0140228 A1 * | 10/2002 | Lacroix | F16L 37/0841 285/317 |
| 2004/0089305 A1 | 5/2004 | Vallarta et al. | |
| 2005/0012330 A1 * | 1/2005 | Schmidt | F16L 37/0841 285/317 |
| 2005/0209581 A1 | 9/2005 | Butts et al. | |
| 2006/0180219 A1 | 8/2006 | Jeong | |
| 2006/0271015 A1 | 11/2006 | Mantell | |
| 2007/0209716 A1 * | 9/2007 | Rankin | F16K 37/0033 137/554 |
| 2008/0000472 A1 * | 1/2008 | Wall | A61M 16/20 128/202.27 |
| 2008/0061553 A1 | 3/2008 | Schmidt | |
| 2009/0284007 A1 | 11/2009 | Schmidt | |
| 2012/0153615 A1 * | 6/2012 | Rehder | F16L 37/0841 285/399 |
| 2013/0014757 A1 | 1/2013 | McPhearson | |
| 2013/0333767 A1 * | 12/2013 | Schmidt | F16L 37/35 137/15.18 |
| 2015/0343195 A1 | 12/2015 | Laufer | |
| 2016/0100784 A1 | 4/2016 | Kashmirian | |
| 2016/0131292 A1 | 5/2016 | Decker | |
| 2016/0199602 A1 | 7/2016 | Fernandez | |
| 2017/0246362 A1 | 8/2017 | Crawford | |

OTHER PUBLICATIONS

Youtube.com, SMT Oxygen Flow Adapter, Aug. 15, 2017, https://smt-medical.net/technology2 (Year: 2017).

* cited by examiner

OXYGEN SUPPLY QUICK CONNECT ADAPTER

This application is a continuation-in-part of U.S. patent application Ser. No. 14/537,158, filed Nov. 10, 2014, and this application also claims the benefits under 35 U.S.C. § 119(e) of U.S. Provisional Patent Application No. 62/328,229 filed Apr. 27, 2016, each of the above-identified applications are fully incorporated herein by reference.

BACKGROUND OF THE INVENTION

Field of the Invention

Embodiments disclosed herein relate to an oxygen supply system, and more particularly to a method, device and system for an oxygen supply quick connect adapter.

Discussion of the Related Art

Medical piped fluid systems in hospitals, and most other healthcare facilities, are used for supplying piped oxygen and other gases (or fluids) from an oxygen source to various parts of a hospital, including standard hospital room (operating, procedure or other rooms) oxygen line outlets. In typical hospital rooms, oxygen outlet(s) are colored green and located near the patient bed or procedure table. Most standard hospital bed rooms have at least two (2) oxygen outlets, and also a yellow outlet that represents "room air." Intensive care, operating, and other procedure rooms may have multiple oxygen and air outlets that are needed not only for basic respiratory equipment, but also life support machines (e.g., ventilators, cardiopulmonary bypass pumps, etc.). Attached at the outlet, a Thorpe Tube, or other flow-meter, reduces the pressure from bulk storage (at the wall) to "working" pressure (e.g., 50 psi). The Thorpe Tube flow-meter then regulates the flow through the use of a knob that is turned counter clockwise or clockwise to achieve the desired flow rate.

Resuscitation or "ambu" bags, face masks, nebulizers, nasal cannulas and other oxygen delivery devices typically have tubing that attaches to a nipple or "Christmas tree" connector on the flow-meter to facilitate connection to the oxygen source. Christmas tree connectors have deep grooved barbs over which the oxygen tubing slides. These connectors facilitate a rapid mechanical connection and disconnection (e.g., push the tubing on or pull the tubing off), by hand, to oxygen sources. Christmas tree connectors have a threaded end that screws onto the flow-meter outlet.

However, rapid connection and disconnection of oxygen tubing from the Christmas tree connectors has long led to excessive oxygen waste. Most notably, even after oxygen tubing is disconnected from the Christmas tree connector, oxygen sources are often left running at various flow rates for hours or even days. Often times this occurs because hospital staff is in a hurry, or simply neglects to turn off the oxygen source. In any event, oxygen continues to bleed for extended periods of time leading to excessive waste. This has been documented over a long period of time and numerous healthcare professionals have expressed a long felt need to control or stop oxygen waste. Oxygen waste in hospitals is widely acknowledged, but, yet to be addressed. A 2010 study found that fifteen (15) operating rooms wasted roughly 19,000 L of oxygen, or about 670 cubic feet, in a five-day span, which extrapolated over a one year period amounted to nearly one million liters in wasted oxygen.

In addition, Christmas tree connectors do not maintain current oxygen flow rates once disconnected. That is, when patients are transferred from location to location (e.g., discharged or leaves the room for testing or other procedure), their flow oxygen rates, if turned off as required, must be reset to proper levels at the new location.

What is needed then is a device to overcome the deficiencies of the prior art and address these long felt needs.

SUMMARY OF THE INVENTION

Accordingly, the invention is directed to a quick connect assembly, insert assembly, method of making and using a quick connect assembly, insert assembly, method of making and using the same that substantially obviates one or more of the problems due to limitations and disadvantages of the related art.

An advantage of the invention is to provide a device configured to reduce excessive oxygen waste throughout hospitals, outpatient surgery centers, long term care facilities, and the like.

Another advantage of the invention is to provide a device with safety features for patients utilizing oxygen therapy with features to eliminate the need for multiple staff adjusting prescribed oxygen flow settings pre and post transport.

Yet another advantage of the invention is a device designed to halt oxygen flow mechanically, by push button release, rather than manually (turning a knob) and returns the correct setting when reconnected, thus eliminating the need to readjust prescribed oxygen settings upon patient return from transport or discharge.

Yet another advantage of the invention is a device that allows for connection to one or more secondary devices, e.g., humidifiers (in-line or not in-line) with an oxygen supply source.

Still yet another advantage, the quick connect device allows easy "one-hand" connect and disconnect by simply depressing the catch device. The quick connect device is made of materials that are resistant to chemicals and oxygen, e.g., thermoplastic material, stainless steel, combinations of the same. Most importantly, the quick connect device addresses a long felt need in the medical industry to eliminate oxygen waste by shutting off the oxygen flow when the male insert having oxygen tubing attached thereto is removed from the female coupling. When the quick connect assembly is reconnected to the insert, the oxygen begins to flow at the rate previously set. In this manner, the desired, previously set oxygen flow rate is maintained. To summarize, when the male insert is not connected to the female coupling, oxygen does not flow; when the male insert is connected to the female coupling, oxygen flows at a consistent rate previously set. This avoids errors as compared to the related art by not requiring turning off the oxygen and then turning it back on and manually readjusting. Moreover, it mitigates waste as typically the oxygen is not turned off in the related art and when a product is disengaged oxygen flows without purpose into the room.

Additional features and advantages of the invention will be set forth in the description which follows, and in part will be apparent from the description, or may be learned by practice of the invention. The objectives and other advantages of the invention will be realized and attained by the structure particularly pointed out in the written description and claims hereof as well as the appended drawings.

In one embodiment, a method of using a quick-connect assembly for use with an oxygen gas supply source includes obtaining a quick-connect assembly including a cylindrical main body having a first end, a second end and a longitudinal bore extending from the first end to the second end. The first end includes a quick-connection mechanism configured to accept an insert assembly and the second end comprises an attachment mechanism. The method further includes connecting the second end to the oxygen gas supply source and obtaining an insert assembly including a body having a first end, a second end and a longitudinal bore extending from the first end to the second end, a circumferential grove is arranged proximal to the first end and is configured to engage the quick-connection mechanism. Next, arranging the first end of the insert assembly into the first end of the quick-connection assembly and engaging the quick-connection mechanism with the circumferential grove to releasably couple the insert assembly to the quick-connect assembly.

In another embodiment, the method includes using a quick-connect assembly for use with an oxygen gas supply source includes obtaining a quick-connect assembly including a cylindrical main body having a first end, a second end, a longitudinal bore extending from the first end to the second end, and one or more sensors, wherein the first end comprises a quick-connection mechanism configured to accept an insert assembly and the second end comprises an attachment mechanism. Next, the method includes connecting the second end to the oxygen gas supply source and obtaining an insert assembly including a body having a first end, a second end and a longitudinal bore extending from the first end to the second end, a circumferential grove is arranged proximal to the first end and is configured to engage the quick-connection mechanism. Next, the method includes arranging the first end of the insert assembly into the first end of the quick-connection assembly and engaging the quick-connection mechanism with the circumferential grove to releasably couple the insert assembly to the quick-connect assembly. In yet another embodiment, the method of using a quick-connect assembly for use with an oxygen gas supply source includes obtaining a quick-connect assembly comprising a cylindrical main body having a first end, a second end, a longitudinal bore extending from the first end to the second end, wherein the first end comprises a catch plate configured to accept an insert assembly and the second end comprises an attachment mechanism, and a biased plunger arranged within the longitudinal bore of the cylindrical main body configured to move from a closed position to an open position, wherein the closed position prevents oxygen gas flow from the oxygen gas supply source from the second end to the first end, and wherein the open position permits oxygen gas flow, the oxygen gas supply source from the second end to the first end when the oxygen gas supply source is on and the second end is connected to the oxygen gas supply source. Next, the method includes connecting the second end of the quick-connect assembly to the oxygen gas supply source and obtaining an insert assembly comprising a body having a first end, a second end and a longitudinal bore extending from the first end to the second end, a circumferential grove is arranged proximal to the first end and is configured to engage the quick-connection mechanism, and the insert assembly does not include a biased plunger or a seal member. Further the method includes arranging the first end of the insert assembly into the first end of the quick-connection assembly and engaging a portion of the catch plate with the circumferential grove to releasably couple the insert assembly to the quick-connect assembly.

Embodiments described herein overcome the deficiencies and disadvantages of the prior art described above. These deficiencies and disadvantages are overcome, for example, by an oxygen quick-connect device, that includes a female coupling and a male insert. The female coupling has a first end and second end and a bore extending longitudinally through the first and second ends and further includes a biased plunger disposed within the bore of the female coupling and configured to reciprocate within, a seal member disposed on the plunger and configured to seal at a location on the bore of the female coupling, a catch device disposed at a second end of the female coupling body, and means for connecting the female coupling to an oxygen supply source. The male insert has a first end and a second end and a first bore extending longitudinally through the first and second ends and includes a biased plunger disposed within the first bore of the male insert and configured to reciprocate within, a first seal member disposed on the plunger and configured to seal at a location on the first bore of the male insert, a second seal member disposed on the male insert and configured to seal within the bore of the female coupling, and a barbed connection disposed at a second end of the male insert having a second bore extending there-through perpendicular to the first bore of the male insert, in which the second bore has a diameter that enables the quick-connect device to provide a desired flow of oxygen. The oxygen quick-connect device only permits oxygen to flow from the oxygen supply source through the female coupling when the male insert is inserted into the female coupling and the second seal member seals within the bore of the female coupling.

These deficiencies and disadvantages are overcome, for example, by a quick-connect insert having oxygen tubing attached thereto, the quick-connect insert configured to be secured by a catch device on a female coupling in fluid communication with an oxygen source. The quick-connect insert includes a cylindrical main body having a longitudinal bore, a first seal member disposed on an outer diameter of a first end of the main body, in which the first end is insertable within the female coupling to form a fluid seal, a circumferential groove on an outer diameter of the first end configured to engage the catch device, a barbed connector extending perpendicular relative to the main body at a second end, and an orifice extending through the barbed connector, and a movable plunger within the longitudinal bore of the main body configured to allow oxygen to flow from the female coupling and through the orifice of the barbed connector when the quick-connect insert is connected to the female coupling.

This Summary section is neither intended to be, nor should be, construed as being representative of the full extent and scope of the present disclosure. Additional benefits, features and embodiments of the present disclosure are set forth in the attached figures and in the description herein below, and as described by the claims. Accordingly, it should be understood that this Summary section may not contain all of the aspects and embodiments claimed herein.

Additionally, the disclosure herein is not meant to be limiting or restrictive in any manner. Moreover, the present disclosure is intended to provide an understanding to those of ordinary skill in the art of one or more representative embodiments supporting the claims. Thus, it is important that the claims be regarded as having a scope including constructions of various features of the present disclosure insofar as they do not depart from the scope of the methods and apparatuses consistent with the present disclosure (including the originally filed claims). Moreover, the present disclosure is intended to encompass and include obvious improvements and modifications of the present disclosure.

BRIEF DESCRIPTION OF THE DRAWINGS

The accompanying drawings, which are included to provide a further understanding of the invention and are incorporated in and constitute a part of this specification, illustrate embodiments of the invention and together with the description serve to explain the principles of the invention.

In the drawings.

DETAILED DESCRIPTION OF THE ILLUSTRATED EMBODIMENTS

Figure 1:
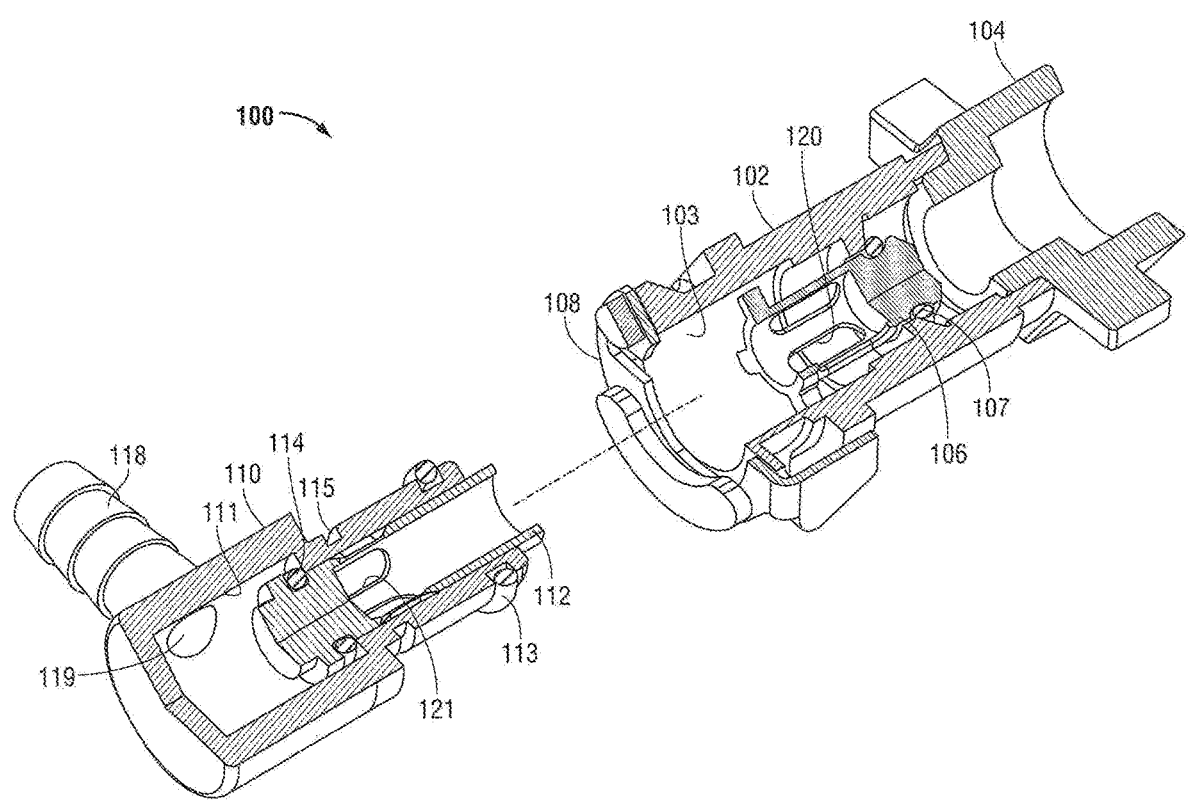
FIG. 1 illustrates a cutaway view of an embodiment of a disassembled oxygen quick-connect.

As used herein, "comprising," "including," "containing," "is," "are," "characterized by," and grammatical equivalents thereof are inclusive or open-ended terms that do not exclude additional unrecited elements or method steps unless explicitly stated otherwise.

In order to more fully appreciate the present disclosure and to provide additional related features, the following references are incorporated herein by reference in their entirety:

U.S. Pat. No. 3,450,424 by Calisher which is directed towards a quick connect and disconnect coupling having inter-engaging male and female coupling parts, and a resilient locking member which includes a pair of locking arms straddling and rotatable relative to the female part between a locking position, wherein the arms project laterally through diametrically opposed chordal openings in the female part into an external locking groove in the male part to lock the coupling parts against axial separation, and an unlocking position, wherein the arms straddle and are spread to disengage the male part by intervening body sections on the female part between the chordal openings.

U.S. Pat. No. 4,576,359 by Oetiker, which is directed towards a coupling for lines carrying gas under pressure in which a tubularly shaped male member is adapted to be inserted into a bore of a sleeve-like female member containing a valve assembly automatically opened upon insertion of the tubularly shaped male member. The tubularly shaped male member which is provided with an annular groove is held in its inserted position by a locking mechanism in the sleeve-like female member which consists of a latching member, a ring-like member surrounding the sleeve-like female member and a spring between the latching member and the ring-like member. For purposes of releasing the locking action of the latching member which is operable to engage in the annular groove by movement in a milled-in recess, the ring-like member is provided with an inwardly projecting actuating element. To permit a reduction in the dimensions of the ring-like member, the latching member includes a short leg portion bent with respect to the main portion of the latching member at such angle as to point toward the actuating member.

U.S. Pat. No. 6,581,386 by Young, et al., which is directed towards a combustor baffle, includes an outer tube with external threads and a heat shield at opposite ends thereof. An inner tube is disposed inside the outer tube in a unitary assembly therewith. The outer tube is retained in a combustor dome by a retention nut, and the inner tube supports an air swirler with a brazed joint therewith. The brazed joint permits sacrifice of the baffle during disassembly for access to the threaded joint for final disassembly without damage to the dome or air swirler.

U.S. Pat. No. 7,434,842 by Schmidt, which is directed towards a coupling apparatus having a coupling body with a mechanical latch assembly. The mechanical latch assembly includes a modified latch plate. The latch plate defines a main portion having a top end and a bottom end and includes an annular aperture disposed between the top and bottom ends. A lever portion is disposed proximate the top end. The lever portion enables the latch plate to move within a coupling body, so as to operate the mechanical latch assembly in a released position and a latched position. A raised edge is disposed about a portion of the annular aperture. The raised edge is disposed proximate to the bottom end and extends radially inward of the inner edge defined by the annular aperture. A pin opening is disposed proximate the bottom end opposite of the lever portion. The pin opening is positioned radially outward from the annular aperture, and defines a separate enclosed edge.

Currently, hospitals experience a high rate of oxygen waste using Christmas tree connectors to the oxygen flow control. A quick connect assembly according to embodiments herein is used for eliminating waste by shutting off the oxygen flow when an oxygen tube is disconnected from the device. When the oxygen disconnect device is reconnected, oxygen flows at the rate previously set without further adjustment.

In one embodiment, the assembly includes a female coupling body having a first end and a second end and a bore or opening extending longitudinally through the first and second ends. The female coupling body may be a plastic or thermoplastic material, such as acetyl copolymer. The first end includes a connection mechanism (e.g., a threaded connection) configured as needed for connecting to other pieces of fluid transport equipment, such as but not limited to a gas tank, fluid tank or combinations thereof.

In one embodiment, the assembly is an integral piece of a gas regulator, e.g., oxygen gas regulator. In one embodiment, the assembly is an integral piece of a nasal cannula.

In one embodiment, the assembly is used to connect a secondary device to a gas source.

In one embodiment, a kit includes a quick-connect assembly for use with a gas connection and an insert assembly configured to fit within a portion of the quick-connect assembly. Optionally, the kit includes instructions for use.

In one embodiment, the assembly includes an assembly configured to releasably couple to a humidifier for oxygen treatments.

In one embodiment, the assembly is configured to be coupled to a regulator, secondary device, a humidifier, a standard hospital room oxygen line outlet or other source of gas or fluid.

In one embodiment, the assembly includes a biased plunger disposed within the bore of the female coupling and is configured to reciprocate longitudinally within from an open to a closed position. The plunger includes a seal member at a location configured to seal at some location with an inner surface of the bore in a certain position. The second end of the female coupling body includes a catch device slidably mounted within grooves formed in the second end.

In one embodiment, the catch device is spring-loaded and reciprocates within the grooves from an open to a closed position. In a preferred embodiment, the catch device may be made of a metal material, such as stainless steel. The catch device is configured to receive an insert device.

In one embodiment, the insert includes a first end and a second end and a bore or opening extending longitudinally through the first and second ends. The male insert includes a first seal configured to engage and seal within the bore of the female coupling when the male insert is inserted within the bore of the female coupling. A groove is disposed along a length of the male insert and is configured to engage the catch device of the female coupling. The second end of the male insert includes a Christmas tree type connector that extends perpendicularly from the male insert body. The first end of the male insert is inserted into the second end of the female coupling until the catch device engages the groove in the male insert. There is an audible "click" to signal that a proper connection has been established by a catch pin engaging and locking the insert with the quick connect assembly. Optionally, a window is present on the assembly to verify proper engagement with a color when correct alignment or engagement of catch pin has occurred, e.g., a green color. In one embodiment, a proper connection may send out a communication signal to a secondary device, e.g., a wireless communication signal.

Currently, hospitals experience a high rate of oxygen waste using Christmas tree connectors to the oxygen flow control. An oxygen disconnect device is disclosed for eliminating waste by shutting off the oxygen flow when an oxygen tube is disconnected. When the oxygen disconnect device is reconnected, oxygen flows at the rate previously set without further adjustment. This also minimizes errors in flowrates to the patient.

In one embodiment, the insert adapter and/or the quick connect assembly is configured with one or more sensors.

The one or more sensors may be configured to indicate temperature, gas, location, moisture, flowrate, combinations of the same and other information required for patient medical needs.

In one embodiment, the one or more sensors includes a passive radio-frequency identification device (RFID) and/or passive radio-frequency identification device (RFID). The RFID can be arranged with the insert adapter and/or quick connect assembly and the RFID can be used to provide a unique identifier indicative of one or more of location, manufacture, model, security and the like.

In one embodiment, the one or more sensors can be coupled wirelessly, e.g., Bluetooth, and provide real time information about temperature, pressure, moisture, flowrate, location and combinations of the same and other information required for patient medical needs. Moreover, the one or more sensors can be configured to wirelessly communicate with a secondary device on a predetermined event, e.g., where a gas flow rate is below or above a predetermined level. The secondary device may include mobile communication device, computer, server, alarm source, and the like.

In one embodiment, the quick-connect device includes a female coupling body having a first end and second end and a bore or opening extending longitudinally through the first and second ends. Generally the female coupling body may be a plastic or thermoplastic material, such as acetyl copolymer. The first end includes a connection means (e.g., threaded connection) configured as needed for connecting to other pieces of fluid transport equipment such as, but not limited to, a gas or fluid line (e.g., a standard hospital room oxygen line outlet). A first biased plunger is disposed within the bore of the female coupling and is configured to reciprocate longitudinally within. The plunger includes a seal member at a location configured to seal at some location with an inner surface of the bore in a certain position. The second end of the female coupling body includes a catch device slidably mounted within grooves formed in the second end. The catch device is spring-loaded and reciprocates within the grooves. The catch device may be made of a metal material, such as stainless steel.

In one embodiment, the quick-connect device includes a male insert having a first end and second end and a first bore or opening extending longitudinally through the first and second ends. The male insert includes a first seal configured to engage and seal within the bore of the female coupling when the male insert is inserted within the bore of the female coupling. A groove is disposed along a length of the male insert and is configured to engage the catch device of the female coupling when the quick-connect device is assembled, as discussed below. There is no biased plunger is disposed within the first bore of the male insert.

In one embodiment, the first end of the male insert is inserted into the second end of the female coupling until the catch device engages the groove in the male insert. There is an audible "click" to signal that a proper connection has been established by the catch pin engaging with cutout of the catch plate and locking the insert to the female coupling. Upon coupling, the biased plunger of the female coupling engages an end of the male insert and is forced in a direction to unseal a seal member for seal seat on the bore of the coupling and allow fluid communication through the bore of the female coupling and through the bore of the insert. To uncouple or disconnect the male insert from the female coupling, the catch device is depressed to disengage the catch device from the groove in the male insert and disengage the catch pin. When disengaged, the biased plunger of the female coupling moves longitudinally within the bore to engage the seal member with the seal member seat to prevent oxygen flow from the first end of female coupling to the second end of the female coupling. The female coupling is now in the closed orientation.

Figure 2:
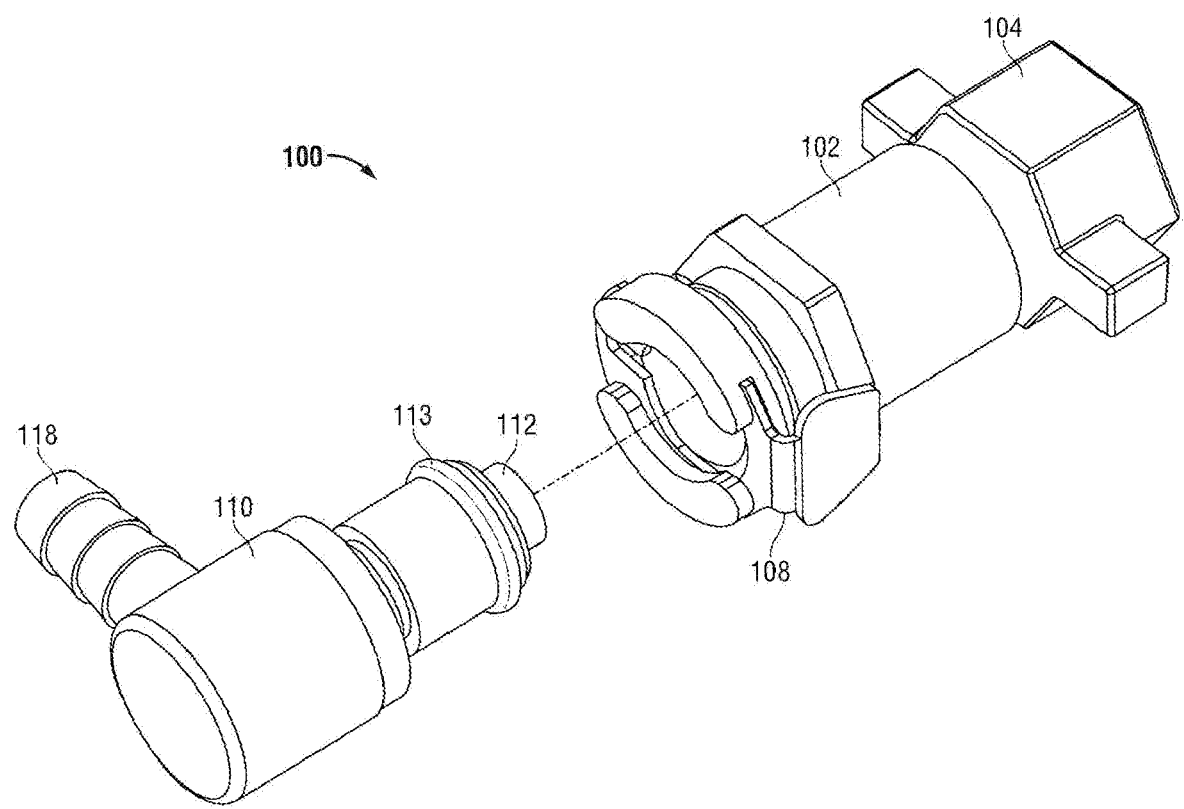
FIG. 2 illustrates a perspective view of an embodiment of a disassembled oxygen quick-connect.

FIGS. 1 and 2 illustrate an embodiment of a disassembled oxygen quick-connect device 100. The quick-connect device 100 includes a female coupling body 102 having a first end and second end and a bore 103 or opening extending longitudinally through the first and second ends. The first end includes a connection means 104 (e.g., a threaded connection) configured as needed for connecting to other pieces of gas or fluid transport equipment (not shown), such as but not limited to a gas or fluid line (e.g., a standard hospital-room oxygen line output). A first biased plunger 106 is disposed within the bore 103 of the female coupling body 102 and is configured to reciprocate longitudinally within. The plunger 106 includes a seal member 107 at a location configured to seal at some location (e.g., a seat) with an inner surface of the bore 103 in a certain position. The plunger 106 has a hollow end having a plurality of windows 120 formed in the wall. The second end of the female coupling body 102 includes a catch device 108 slidably mounted within grooves formed in the second end. The catch device 108 is spring-loaded and reciprocates within the grooves. The catch device 108 includes a tab portion that a user may push against and depress in a first direction the catch device against the spring (not shown).

The quick-connect device 100 includes a male insert 110 having a first end and second end and a first bore 111 or opening extending longitudinally through the first end and to the second end. The male insert 110 includes a first seal member 113 configured to engage and seal within the bore 103 of the female coupling body 102. A circumferential groove 115 is disposed on the male insert 110, which the catch device 108 of the female coupling body 102 engages when the quick-connect device 100 is assembled, as discussed below. A second biased plunger 112 is disposed within the first bore 111 of the male insert 110 and is configured to reciprocate longitudinally within. The plunger 112 may extend beyond the first end of the male insert 110, as shown. The plunger 112 includes a second seal member 114 at a location configured to seal at some location (e.g., a seat) with an inner surface of the first bore 111 in a certain position. The plunger 112 has a hollow end having a plurality of windows 121 formed in the wall.

The second end of the male insert 110 includes a Christmas tree connector 118 that extends perpendicularly from the male insert body 110. The Christmas tree connector 118 includes deep grooved barbs over which the oxygen tubing slides. The Christmas tree connector 118 may be sized accordingly. The Christmas tree connector has a second bore 119 that extends within and that is oriented perpendicular to the first bore 111 of the male insert 110. In embodiments, the second bore 119 typically has a diameter of approximately [0.170"+/−0.001"]. It has been found that this diameter enables the quick-connect device to provide the desired flow of oxygen. It is advantageous to have the Christmas tree connector 118 side-mounted on the male insert 110 for attaching oxygen (or other) tubing and to avoid having the Christmas tree connector 118 advertently breaking off when the tubing is attached or removed or simply by being struck when no tubing is attached.

Figure 3:
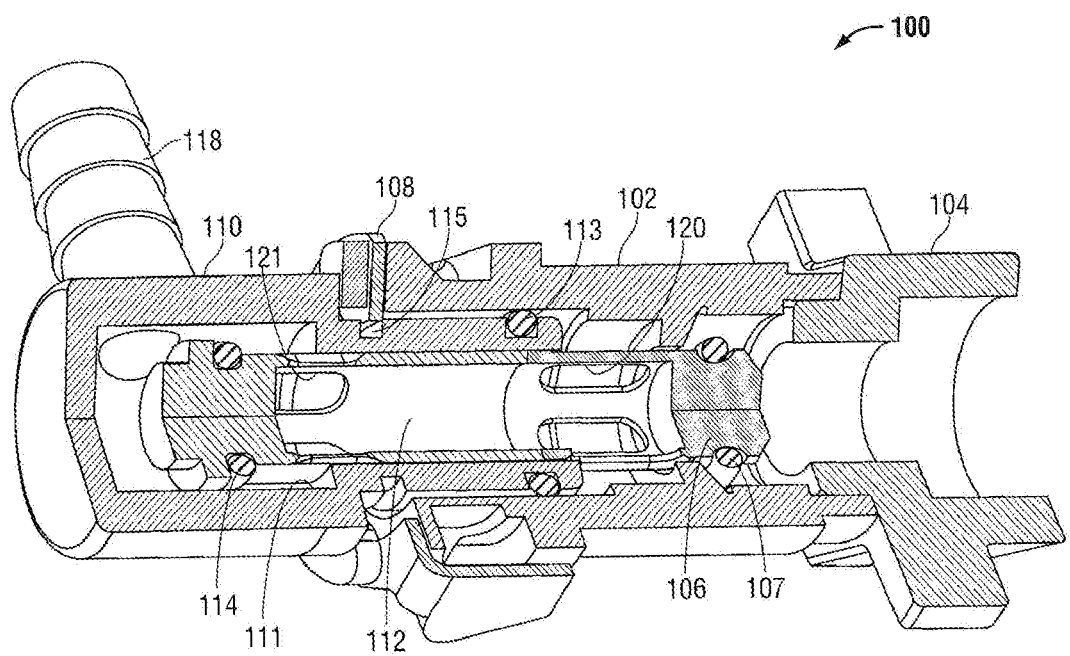
FIG. 3 illustrates a cutaway view of an embodiment of an assembled oxygen quick-connect.
Figure 4:
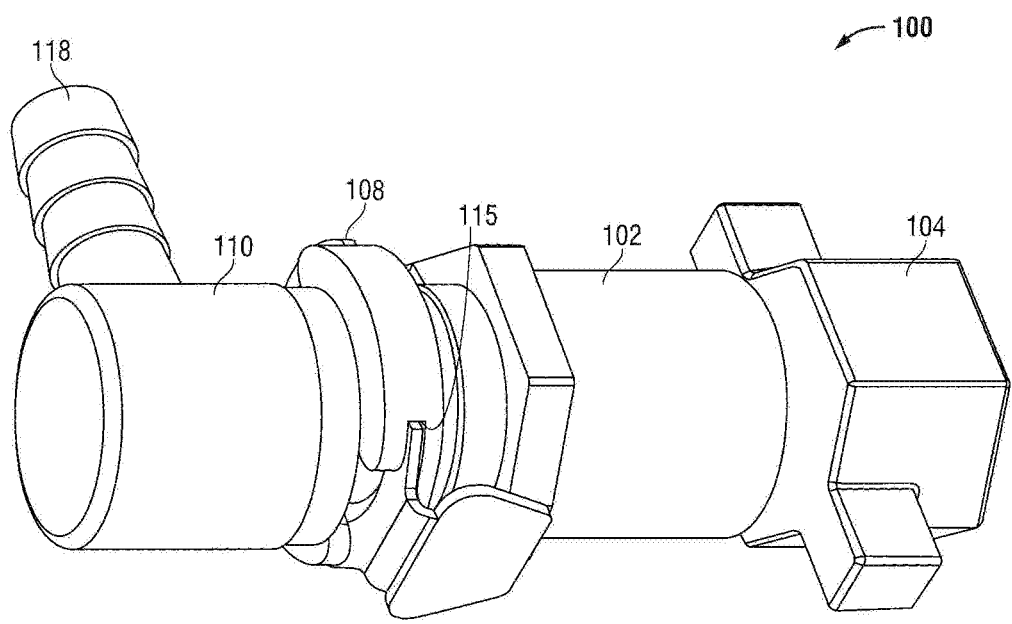
FIG. 4 illustrates a perspective view of an embodiment of an assembled oxygen quick-connect.

FIGS. 3 and 4 illustrate an embodiment of an assembled or connected quick-connect device. The first end of the male insert 110 is inserted into the second end of the female coupling 102, which is connected to a gas or fluid line (e.g., a standard hospital-room oxygen line output) through connection means 104, until the catch device 108 engages the groove 115 in the male insert 110. There is an audible "click" to signal that a proper connection has been established. The seal member 113 on the male insert 110 engages the inner bore 103 of the female coupling 102 to form a seal. Upon coupling, the biased plunger 106 in the female coupling 102 and the biased plunger 112 in the male insert 110 engage end to end and force each other in opposite directions. Moving the biased plunger 106 in the female coupling 102 unseats seal member 107 from an inner bore 103 surface and moves the plurality of windows 120 into a position to allow gas or fluid to flow into the hollow end of the plunger 106. Likewise, moving the biased plunger 112 in the male insert 110 unseats seal member 114 from a first bore 111 surface and moves the plurality of windows 121 into a position to allow fluid to flow into the hollow end of the plunger 110.

Unseating seal members 107 and 114 substantially together allows gas or fluid communication through the quick-connect device 100. That is, oxygen flows from the oxygen source (not shown), into the female coupling 102, through the plurality of windows 120 into the hollow end of the plunger 106, into the hollow end of the plunger 112, out of the plurality of windows 121, into the male insert 110, and out of the Christmas tree connector 118 to an oxygen delivery device (not shown). To uncouple or disconnect the male insert 110 from the female coupling 102, the catch device 108 is depressed to disengage the catch device 108 from the groove 115 in the male insert 110. When disengaged, the biased plungers 106 and 112 disengage, and seal members 107 and 114 are re-seated within their respective bores to prevent oxygen flow through the quick-connect device.

Figure 5A:
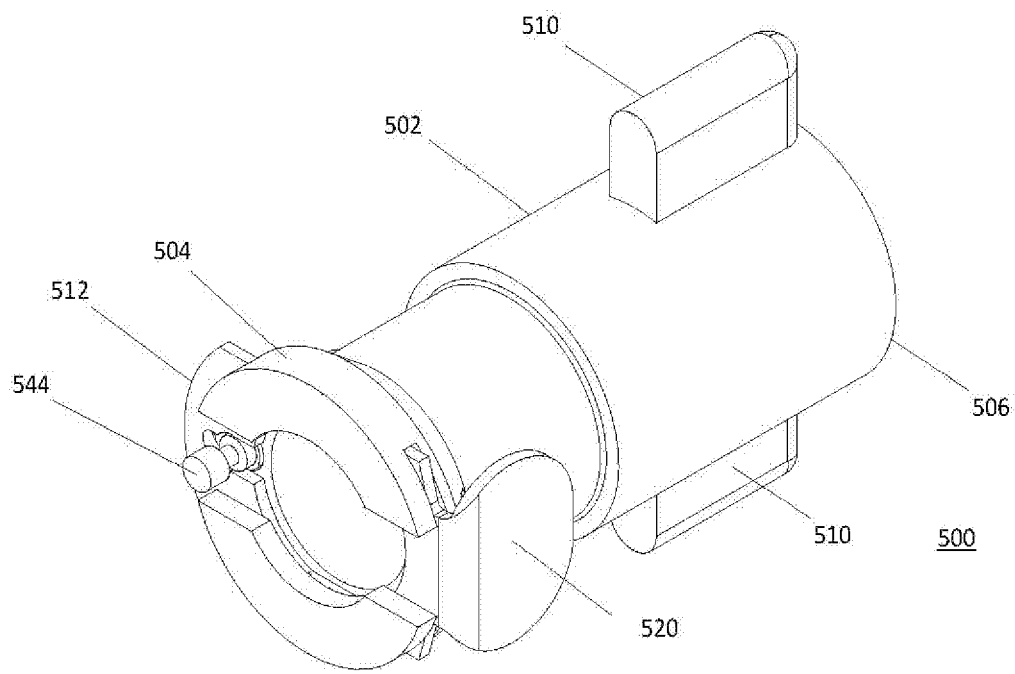
FIG. 5A illustrates a perspective view of an oxygen quick-connect shut off body assembly according to another embodiment of the invention.
Figure 5B:
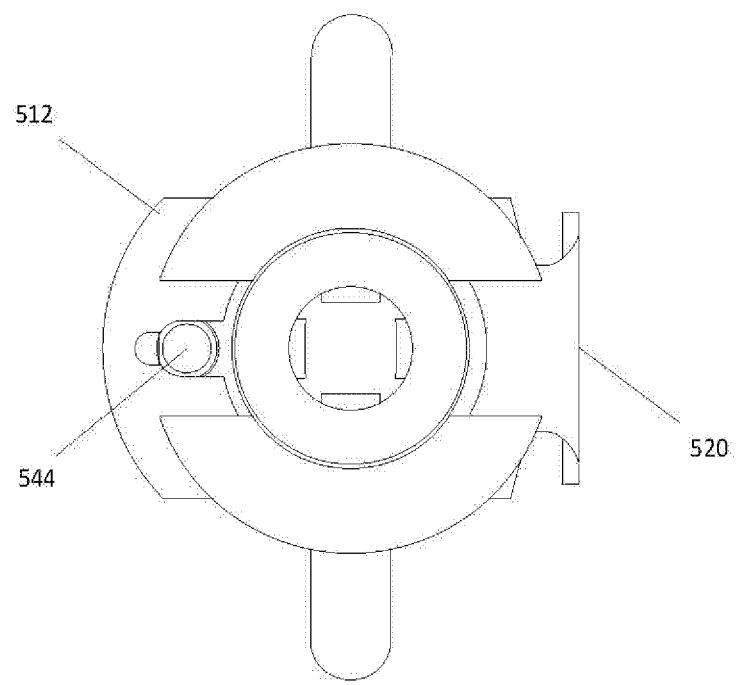
FIG. 5B illustrates a front end view of the oxygen quick-connect shut off body assembly of FIG. 5A.
Figure 5C:
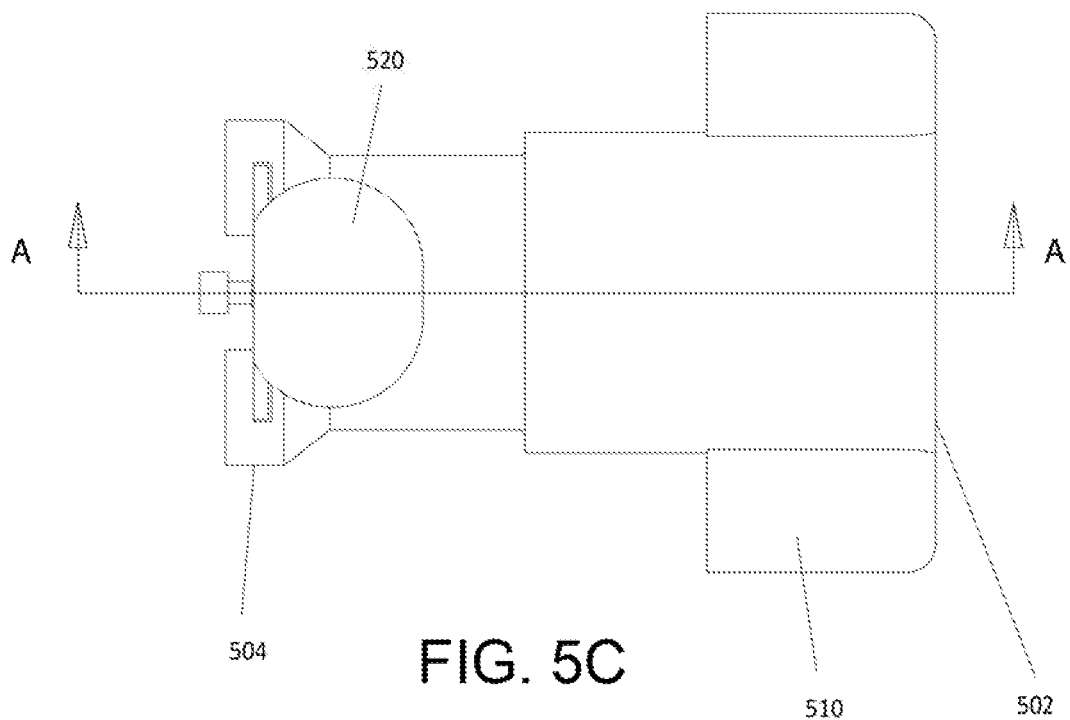
FIG. 5C illustrates a top view of the oxygen quick-connect shut off body assembly of FIG. 5A.
Figure 5D:
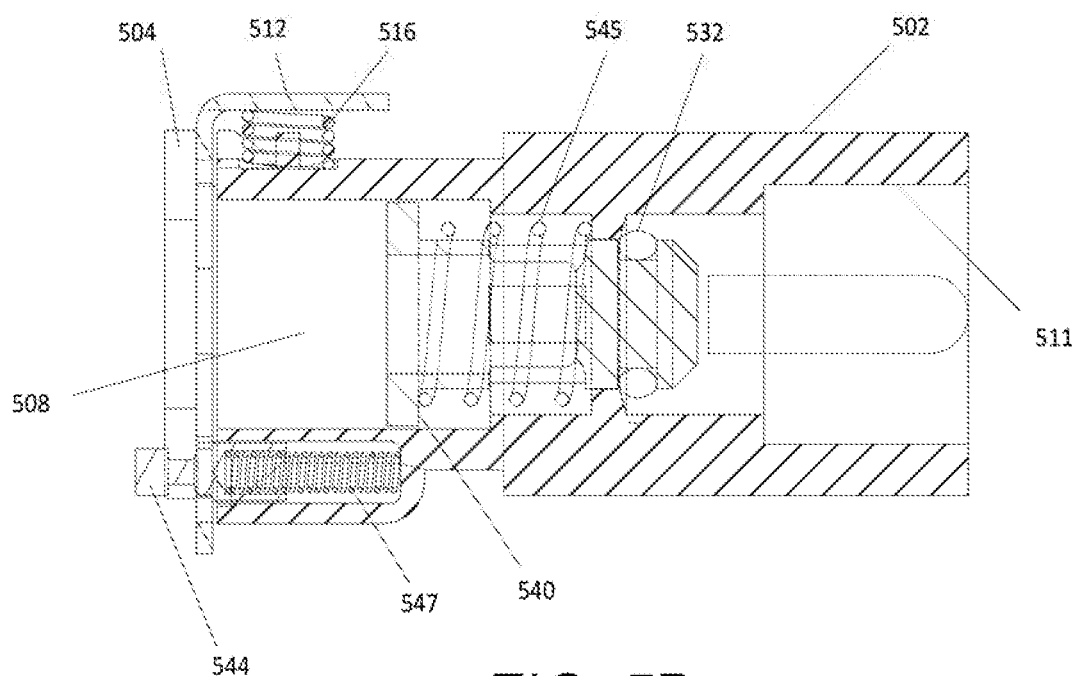
FIG. 5D illustrates a cross-sectional view of FIG. 5C along line A to A.
Figure 5E:
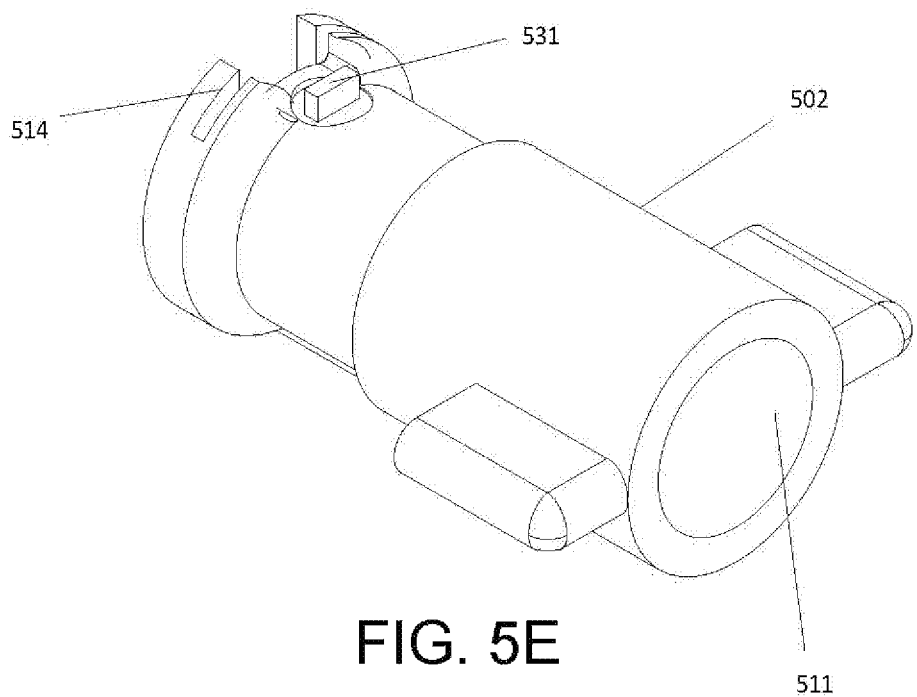
FIG. 5E illustrates bottom rear perspective view of a disassembled oxygen quick-connect shut off body assembly according to FIG. 5A.
Figure 5F:
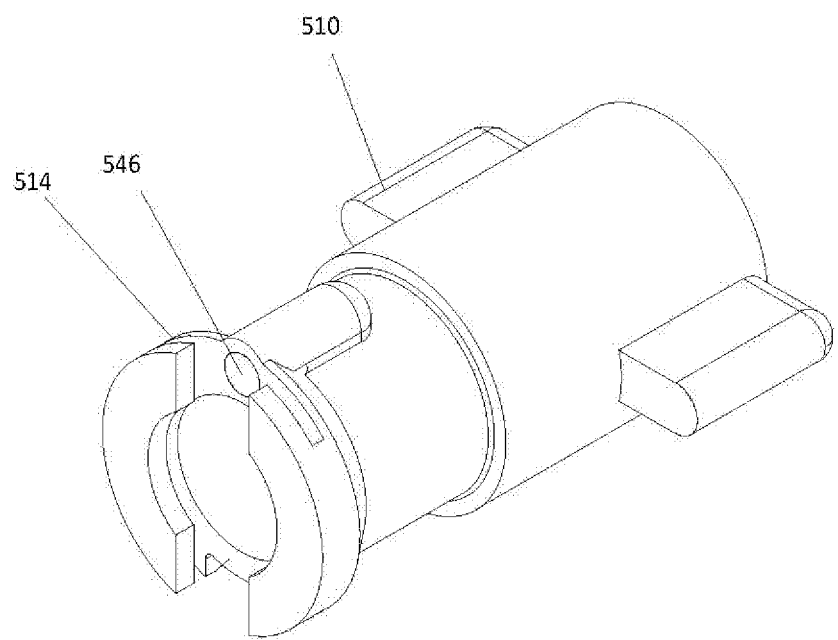
FIG. 5F illustrates top front perspective view of the dissembled oxygen quick-connect according to FIG. 5E.
Figure 5G:
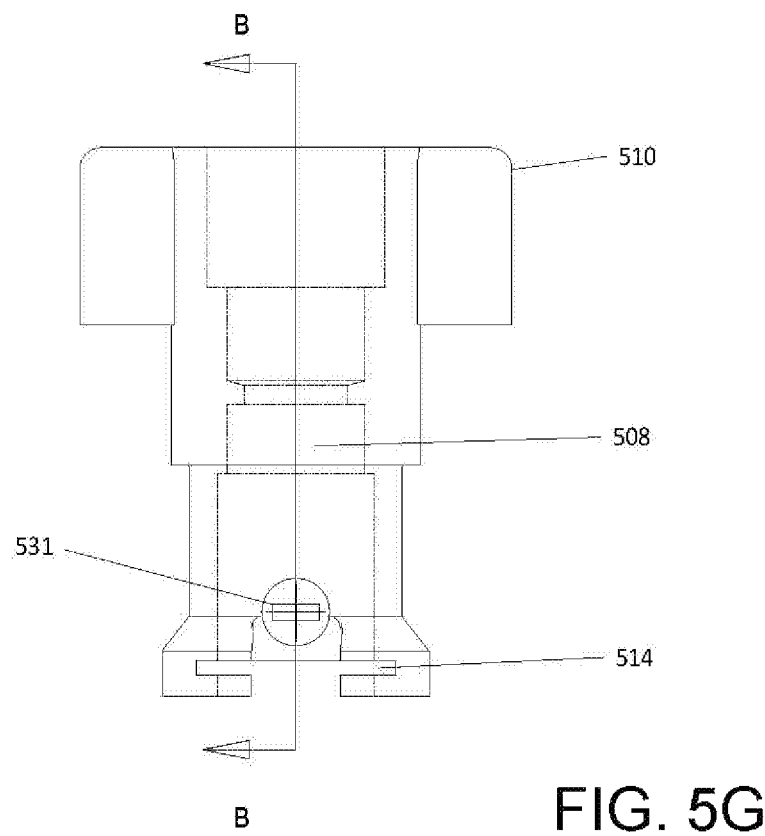
FIG. 5G illustrates top view of a dissembled oxygen quick-connect shut off body assembly according to FIG. 5E.
Figure 5H:
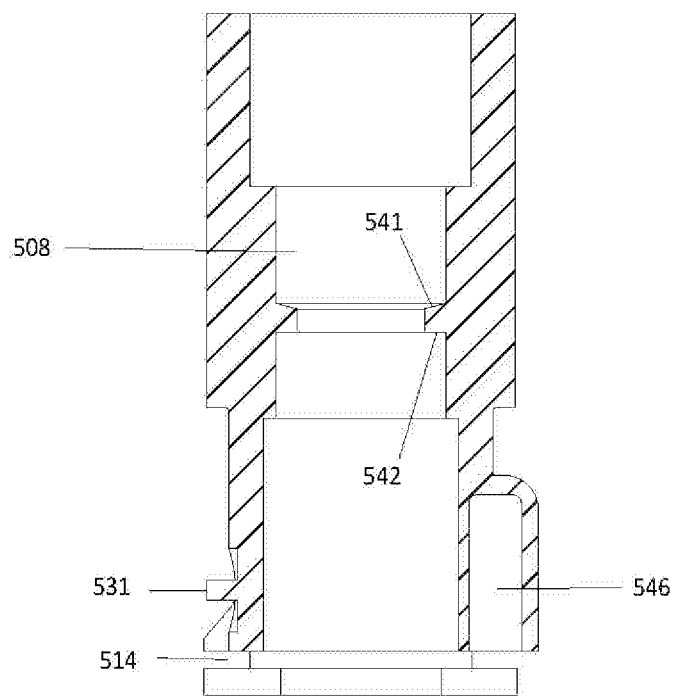
FIG. 5H illustrates cross-sectional view along line B to B of FIG. 5G.
Figure 5I:
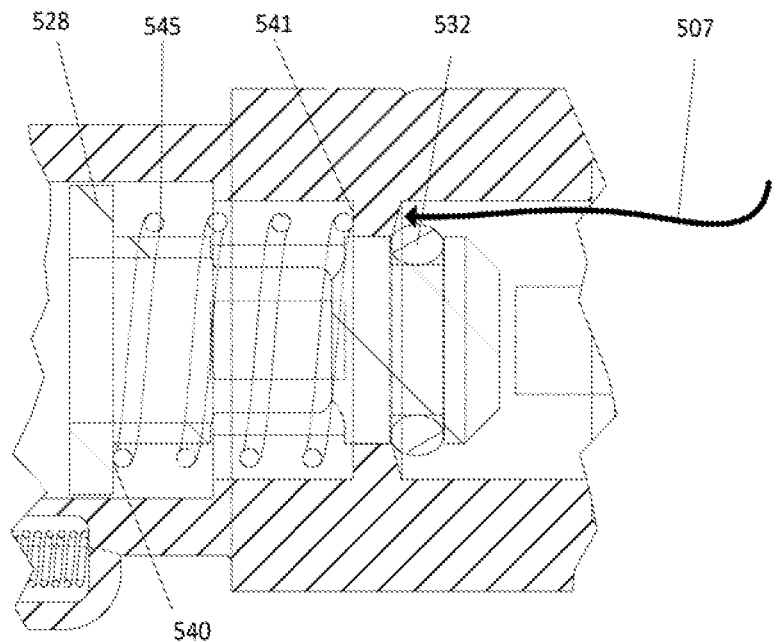
FIG. 5I illustrates an enlarged cross-sectional view of the biased plunger in a closed position.
Figure 5J:
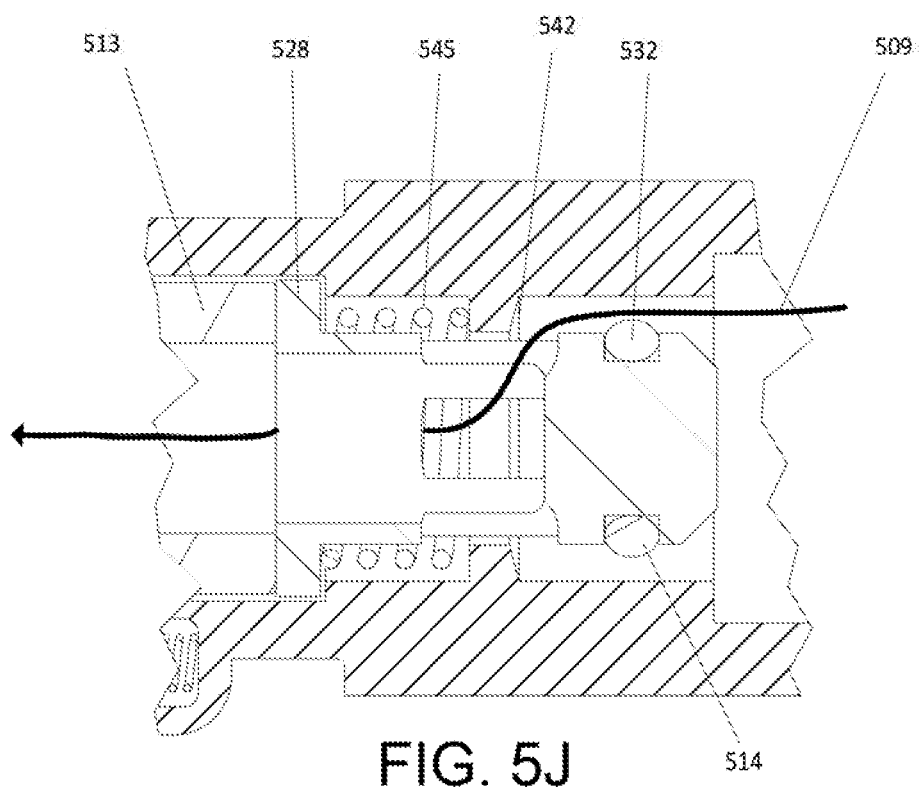
FIG. 5J illustrates an enlarged cross-sectional view of the biased plunger in an open position.
Figure 5K:
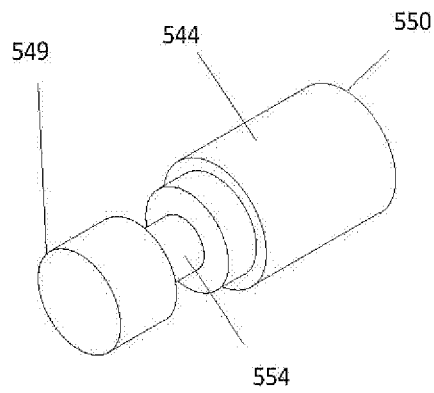
FIG. 5K illustrates a front perspective view of a catch plate pin according to the oxygen quick-connect shut off body assembly of FIG. 5A.
Figure 5L:
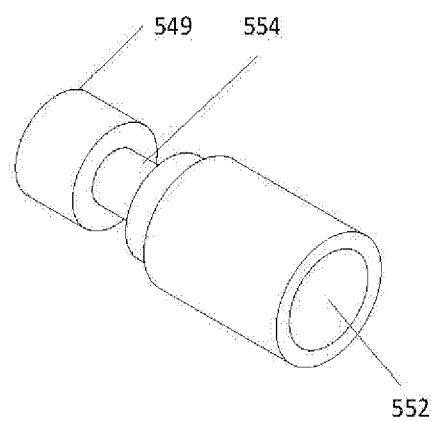
FIG. 5L illustrates a rear perspective view of a catch plate pin according to the oxygen quick-connect shut off body assembly of FIG. 5A.
Figure 5M:
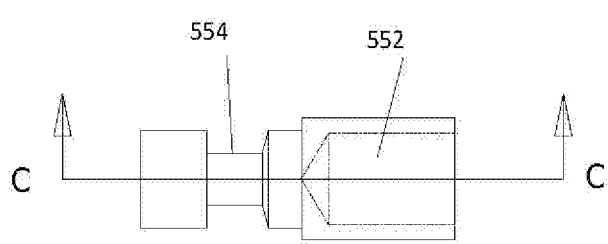
FIG. 5M illustrates a side view of a catch plate pin according to the oxygen quick-connect shut off body assembly of FIG. 5A.
Figure 5N:
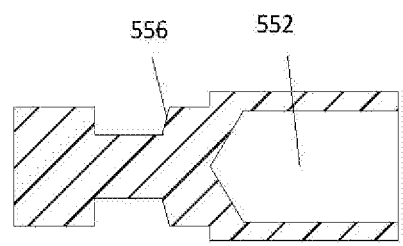
FIG. 5N illustrates a cross-sectional view of FIG. 5M of the catch plate pin along line C to C.
Figure 5O:
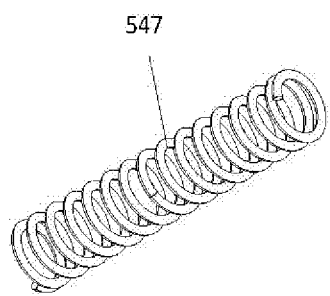
FIG. 5O illustrates a perspective view of a catch plate pin spring according to the oxygen quick-connect shut off body assembly of FIG. 5A.
Figures 5P, 5Q:
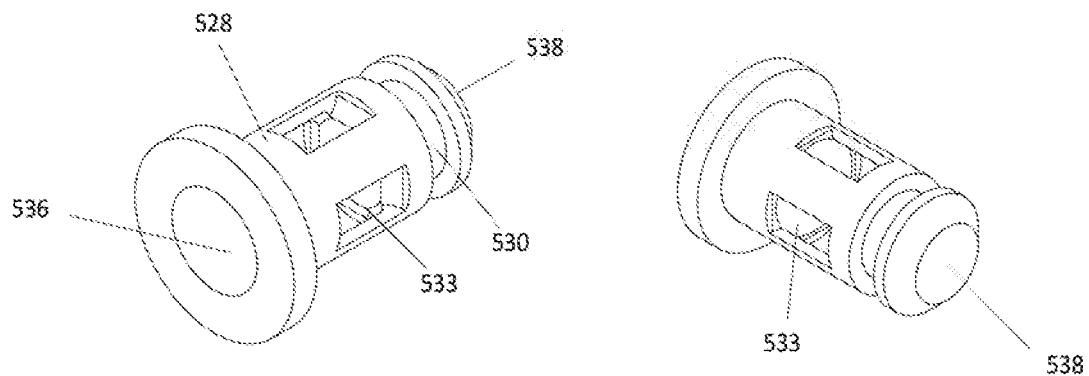
FIG. 5P illustrates a front perspective view of a shut off plunger of the oxygen quick-connect shut off body assembly of FIG. 5A.
FIG. 5Q illustrates a rear perspective view of a shut off plunger of the oxygen quick-connect shut off body assembly of FIG. 5A.
Figures 5R, 5S:
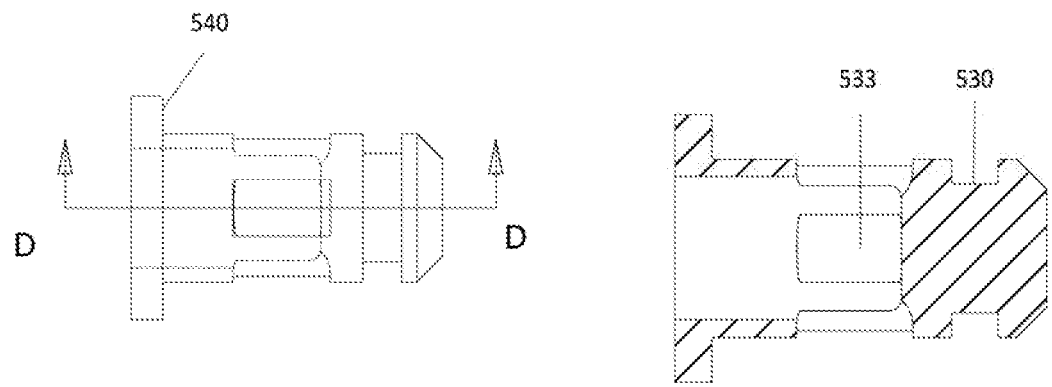
FIG. 5R illustrates a side view of the shut off plunger of the oxygen quick-connect shut off body assembly of FIG. 5A.
FIG. 5S illustrates a cross-sectional view of FIG. 5R along line D to D.
Figure 5T:
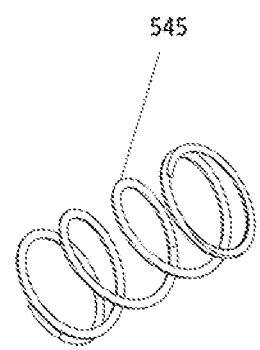
FIG. 5T illustrates a perspective view of a shut off plunger spring of the oxygen quick-connect shut off body assembly of FIG. 5A.
Figure 5U:
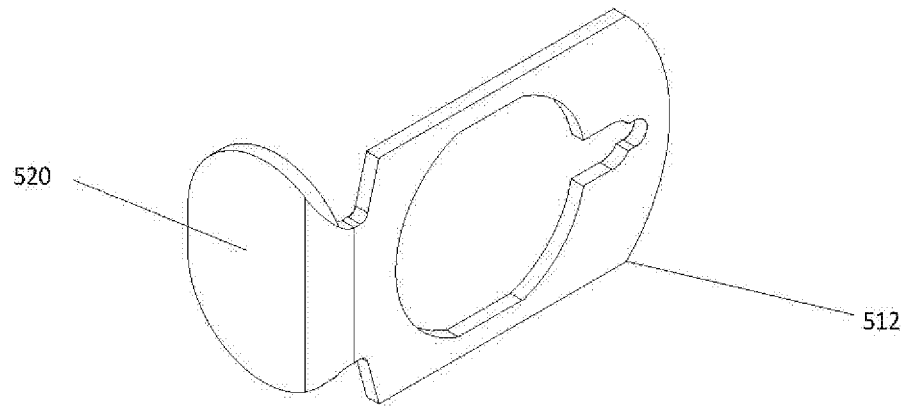
FIG. 5U illustrates a perspective view of a catch plate of the oxygen quick-connect shut off body assembly of FIG. 5A.
Figure 5V:
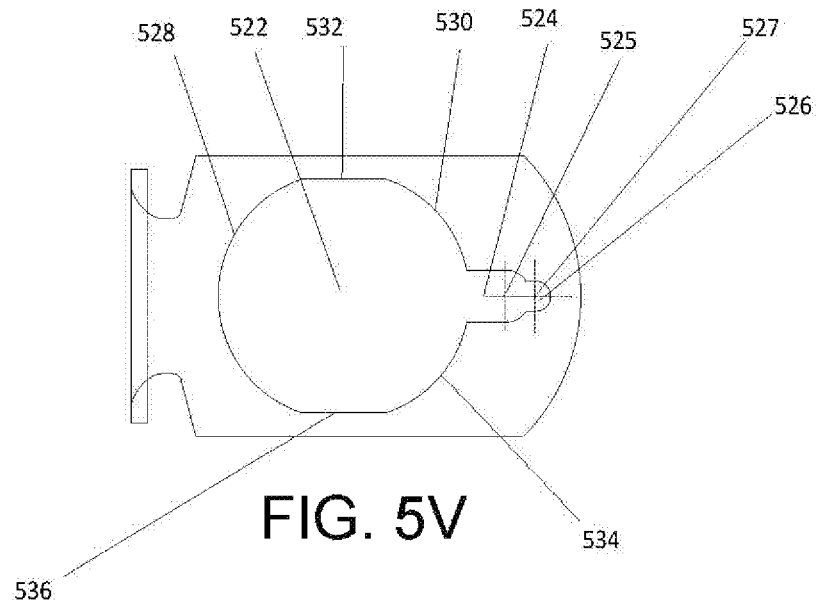
FIG. 5V illustrates a side view of a catch plate of the oxygen quick-connect shut off body assembly of FIG. 5A.
Figure 5W:
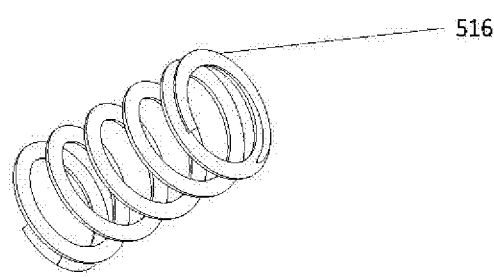
FIG. 5W illustrates a catch plate spring of the oxygen quick-connect shut off body assembly of FIG. 5A.

Referring to FIGS. 5A-5W, an oxygen quick-connect device or shut off body 500 includes a female coupling body 502 having a first end 504, a second end 506 and a bore 508 or opening extending longitudinally through the first and second ends. The second end 506 includes a connection mechanism 511 (e.g., a threaded connection, pressure connection or the like) configured as needed for connecting to other pieces of gas transport equipment, secondary devices or other inserts (not shown), such as but not limited to a gas line (e.g., a standard hospital-room oxygen line output). The second end 506 includes a first and second protrusions 510 configured to assist a user in rotating the shut off body 500 when connecting to other pieces of gas transport equipment.

The first end 504 of includes a quick connect mechanism including a catch device 512 slidably mounted within grooves 514 formed in the first end 504 and catch pin 544. The catch device 512 is biased in an open position with a spring 516 and reciprocates within the grooves 514. The one end of the spring 516 is arranged around a tab portion 531. The catch device 512 includes a tab portion 520 that a user may push against and depress in a first direction the catch device against the spring 516.

Referring to FIGS. 5U-5W, the catch device or catch plate 512 includes cutout portions 522, 524 and 526. The cutout portion 522 includes a half circle geometry 528 connected to a first quarter circle geometry 530 with a straight section 532 having a straight geometry and also connected to a second circle geometry 534 with a straight section 536 having a straight geometry and also connected to a second circle geometry 538. The second cutout portion 524 includes an offset centerline 525. The third cutout portion 526 has a centerline 527. The third cutout 526 is dimensioned to receive a portion of the catch pin in order to lock the adapter with the quick connect assembly 500 as discussed herein.

Referring to FIGS. 5K-5O, the catch pin 544 is configured to fit at least partially within the catch pin channel 546 and biased with a biasing mechanism 547. The biasing mechanism 547 in this embodiment is a spring. The catch pin 544 includes a first end 549 and a second end 550. The second end 550 includes a partial bore section 552 that extends partially and terminates in a wedge shape. In a preferred embodiment, the wedge shape has about a 118 degree angle and configured to seat an end of the spring 547. The bore 552 is configured to receive the biasing mechanism 547. The catch pin 544 includes a recess portion 554 arranged between the first end 549 and second end 550. The recess portion 554 includes an angled portion 556 having about a fifteen degree angle. The angled portion 556 is configured to assist with engaging the catch plate cutout portions 524 and/or 526 when arranging an adapter into the quick connect assembly. The cutout portion 526 is dimensioned such that it can engage the recess 554 of the catch pin 544 in the locked position. The catch pin 544 is configured to reciprocate longitudinally within the recess 546.

Referring to FIGS. 5P-5T, a plunger or shut off plunger 528 is disposed within the bore 508 of the assembly 500 and is configured to reciprocate longitudinally within. The plunger 528 includes a seal member recess 530 arranged to receive a seal member 532 and the seal member 532 is configured to seal at some location (e.g., a seat) with an inner surface of the bore 508 in a certain position. The plunger 528 has a hollow end 536 having a plurality of windows 533 formed in the wall and a closed end 538. A first biasing seat 540 and a second biasing seat 542 are configured to be used with the biasing member 545 thereby creating a biased plunger. The windows 533 and the open end 536 are in gas communication with each other.

FIG. 5I illustrates an enlarged cross-sectional view of the biased plunger in a closed position. FIG. 5J illustrates an enlarged cross-sectional view of the biased plunger in an open position.

Referring to FIGS. 5I and 5J, the biased plunger 528 is biased in a closed position with spring 545 and seat 540 of the plunger and seat 541. The sealing member 532 prevents air flow to exit end 504 as indicated by arrow 507. In an open position the bias plunger 528 is moved by force from the adapter or insert 513, which may be any adapter or insert described herein, from a closed position in FIG. 5I to an open position. Gas flow is now permitted from the second end 506 to the first end 504 of the quick connect assembly end 504 as indicted by the arrow 509. As shown it flows through one or more of the plurality windows 533 out an open end 536 of the plunger and through bore of the adapter.

Figure 6A:
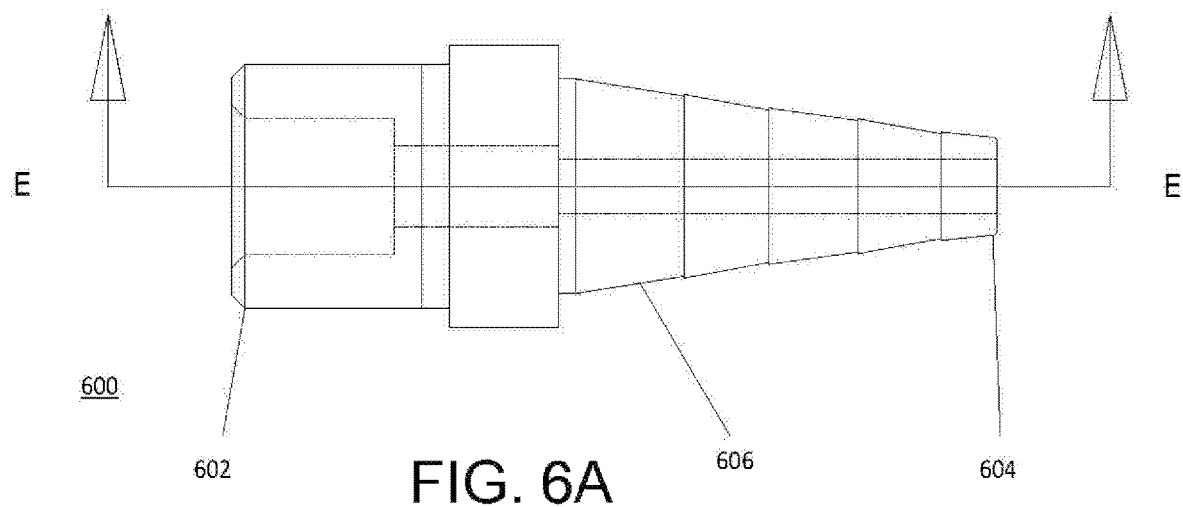
FIG. 6A illustrates a side view of a hose adapter insert according to another embodiment of the invention.
Figure 6B:
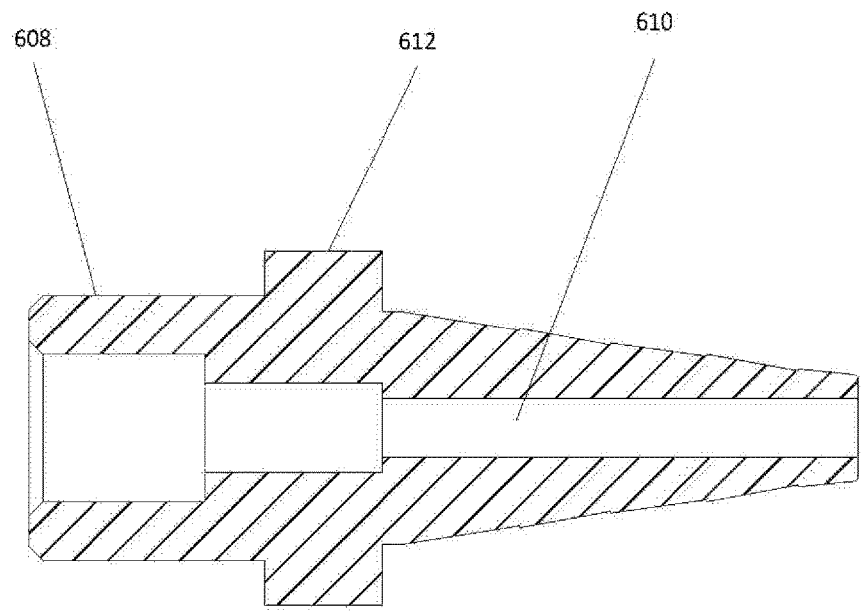
FIG. 6B illustrates a cross-sectional view of FIG. 6A along line E to E.
Figure 6C:
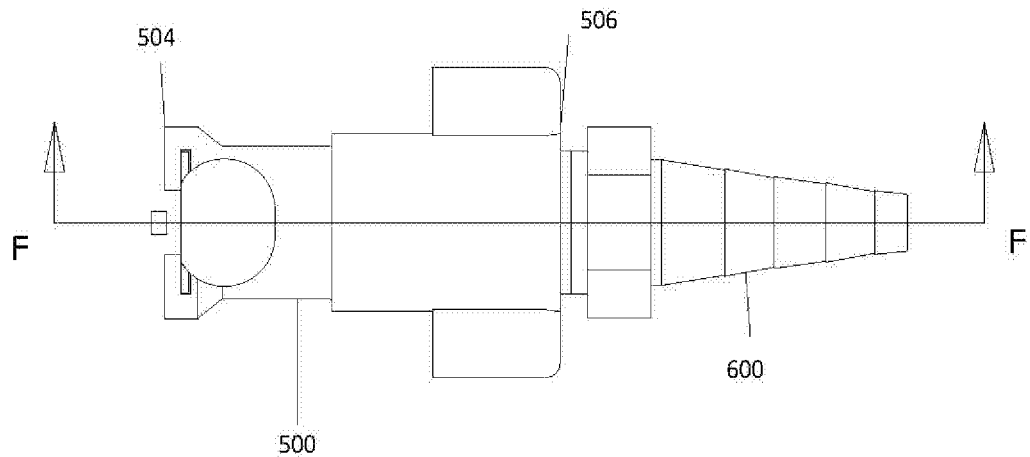
FIG. 6C illustrates an assembled or connected view of the oxygen quick-connect shut off body assembly and the hose adapter insert according to another embodiment of the invention.
Figure 6D:
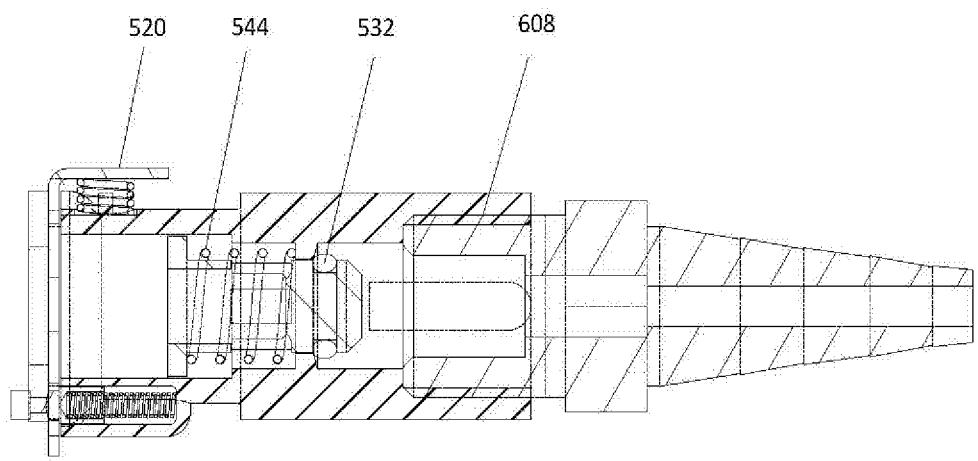
FIG. 6D illustrates a cross-sectional view of FIG. 6C along line F to F.

FIG. 6A illustrates a side view of a hose adapter insert according to another embodiment of the invention. FIG. 6B illustrates a cross-sectional view of FIG. 6A along line E to E. FIG. 6C illustrates an assembled or connected view of the oxygen quick-connect shut off body assembly and the hose adapter insert according to another embodiment of the invention. FIG. 6D illustrates a cross-sectional view of FIG. 6C along line F to F.

Referring to FIGS. 6A-6D, a hose barb adapter 600 has a first end 602 and second end 604 and a bore 610 or opening extending longitudinally through the first end and to the second end. The adapter 600 does not include any seal member. The first end 602 includes a connection mechanism 608 (e.g., a threaded connection, pressure connection or the like) configured to connect to the second end 506 of the quick-connect device 500. In a preferred embodiment, the first end 602 attachment mechanism 608 is configured to engage the connection mechanism 511 of the second end 506 and reside at least partially within the bore 508. Protrusion 612 is configured to assist with rotation of adapter 600. The second end 604 of the barb adapter 600 includes a connector 606 that has a staggered tapper configuration. The connector 606 is includes grooved barbs over which the tubing slides and can become fixedly coupled to the adapter 600 (not shown). When the adapter 600 is releasably coupled to the shut off body 500 the bore 508 of the shut off body 500 and bore 610 of the adapter are in communication with each other thereby allowing gas to flow from the second end 604 through the first end 506 when the plunger 528 is in the open configuration. When the plunger 528 is in the closed configuration (FIG. 5I) there is no flow of gas.

Figure 7A:
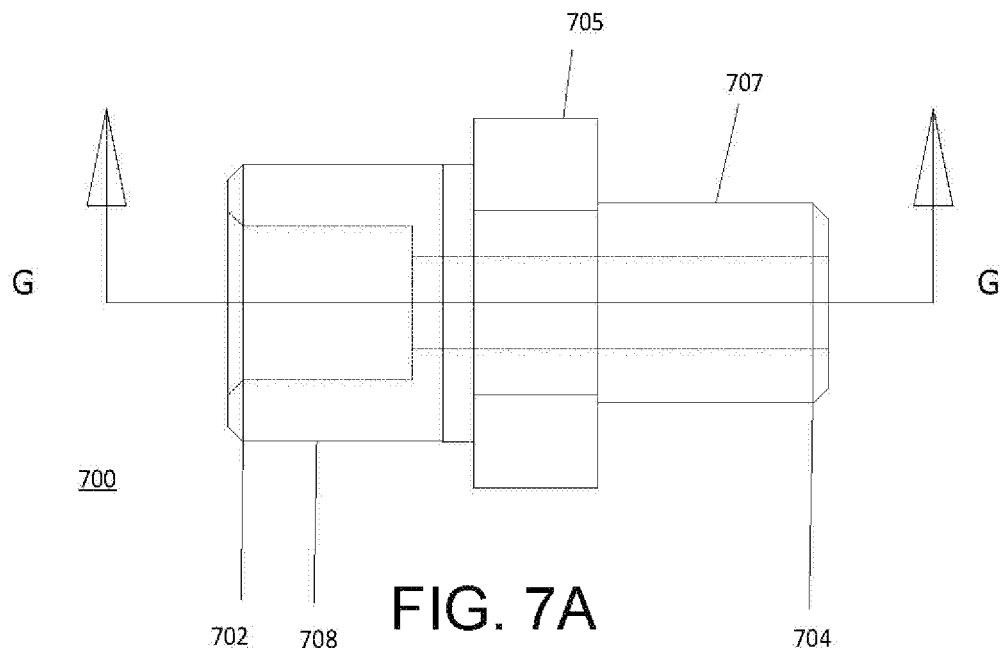
FIG. 7A illustrates a side view of a regulator adapter insert according to another embodiment of the invention.
Figure 7B:
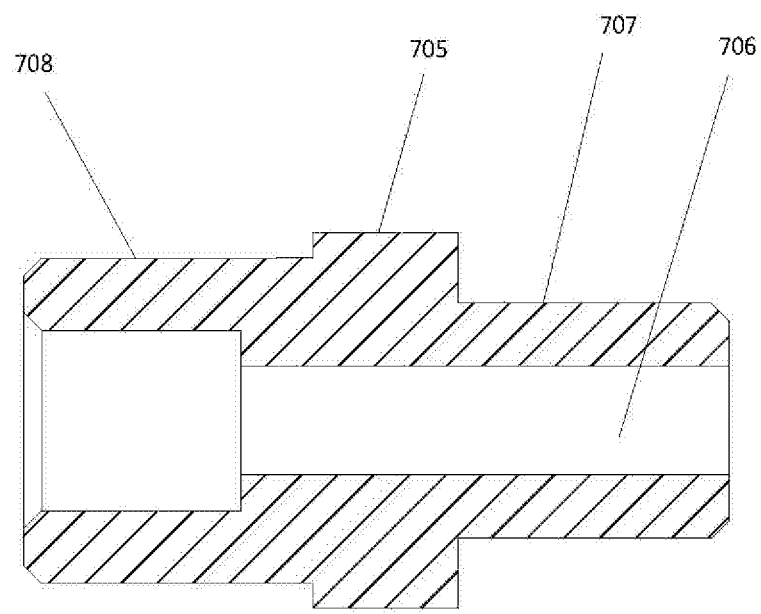
FIG. 7B illustrates a cross-sectional view of FIG. 7A along line G to G.
Figure 7C:
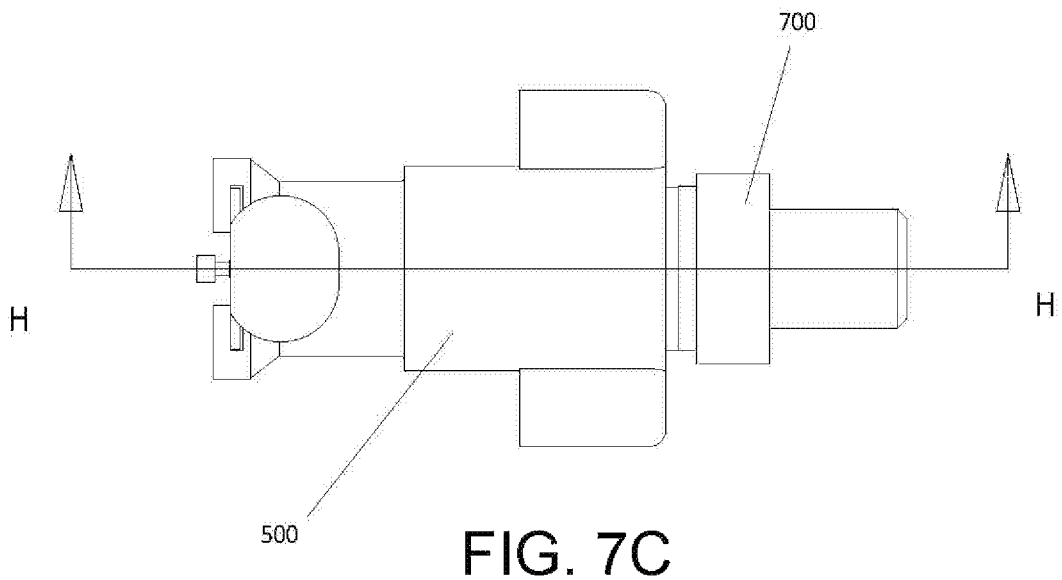
FIG. 7C illustrates an assembled or connected view of the oxygen quick-connect shut off body assembly and the regulator adapter insert according to another embodiment of the invention.
Figure 7D:
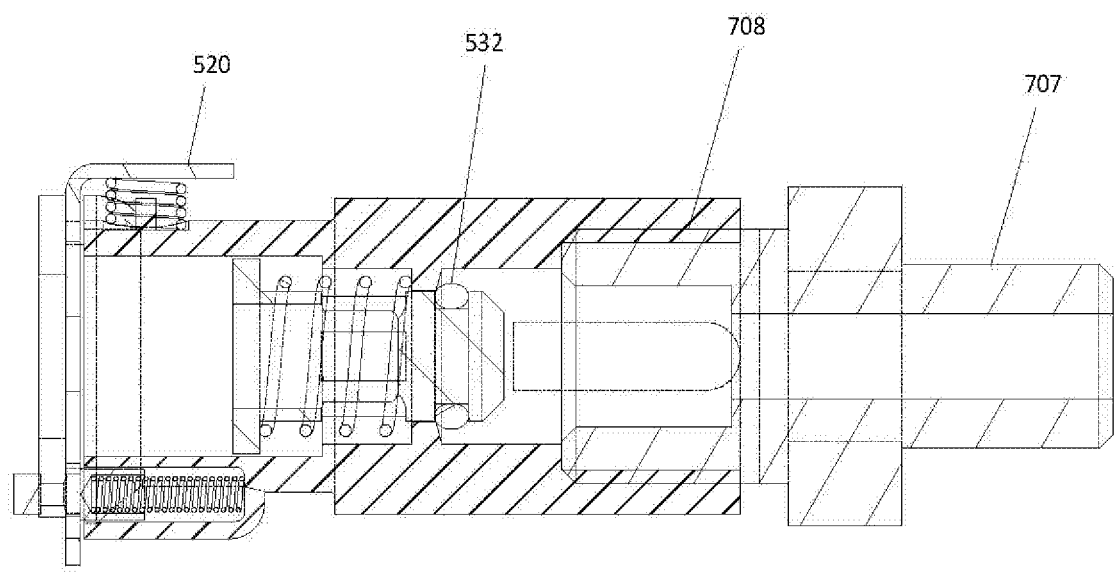
FIG. 7D illustrates a cross-sectional view of FIG. 7C along line H to H.

FIG. 7A illustrates a side view of a regulator adapter insert according to another embodiment of the invention. FIG. 7B illustrates a cross-sectional view of FIG. 7A along line G to G. FIG. 7C illustrates an assembled or connected view of the oxygen quick-connect shut off body assembly and the regulator adapter insert according to another embodiment of the invention. FIG. 7D illustrates a cross-sectional view of FIG. 7C along line H to H.

Referring to FIGS. 7A-7D, a regulator adapter 700 has a first end 702 and second end 704 and a bore 706 or opening extending longitudinally through the first end 702 and to the second end 704. The adapter 700 does not include any seal member. The first end 702 includes a connection mechanism 708 (e.g., a threaded connection, pressure connection or the like) configured to connect to the second end 506 of the quick-connect device 500 or other secondary device. The second end 704 includes a connection mechanism 707 (e.g., a threaded connection, pressure connection or the like) configured to connect to a regulator. A protrusion 705 is configured to assist with rotation of the adapter. In a preferred embodiment, the regulator adapter 700 comprises 304 stainless steel.

In a preferred embodiment, the first end 702 connection mechanism 708 is configured to engage the connection mechanism 510 of the second end 506 and reside at least partially within the bore 508. When the adapter 700 is releasably coupled to the shut off body 500 the bore 508 of the shut off body 500 and bore 706 of the adapter 700 are in communication with each other thereby allowing gas to flow from the second end 704 through the second end 504 when the plunger 528 is in the open configuration. When the plunger 528 is in the closed configuration there is no flow of gas.

Figure 8A:
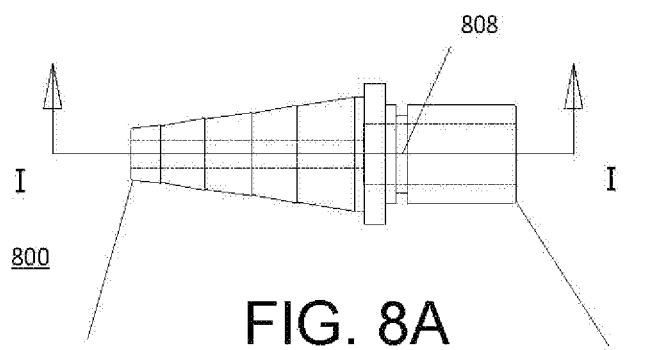
FIG. 8A illustrates a side view of an adapter insert according to another embodiment of the invention.
Figure 8B:
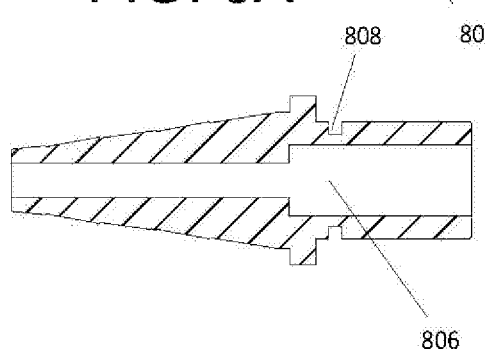
FIG. 8B illustrates a cross-sectional view of FIG. 8A along line I to I.

FIG. 8A illustrates a side view of an adapter insert according to another embodiment of the invention. FIG. 8B illustrates a cross-sectional view of FIG. 8A along line I to I.

Referring to FIGS. 8A-8B, a hose barb adapter 800 includes a first end 802, a second end 804 and a first bore 806 or opening extending longitudinally through the first end 802 and to the second end 804. The male insert 800 includes a circumferential groove 808 disposed on the insert 800, which the catch device 512 of the shut off body 500 engages when the shut off body 500 is assembled with the insert 800. The insert 800 does not include a seal member, e.g., O-ring. The second end 804 of the male insert includes a Christmas tree connector 810 that extends perpendicularly from the male insert body. The Christmas tree connector 810 includes deep grooved barbs over which the oxygen tubing slides. The Christmas tree connector 810 may be sized to receive a range of diameter of tubing. The second end 804 is configured in a tapered configuration with a Christmas tree type shape. The tapered configuration has a plurality staggered or grooved barbs over which the tubing slides and can become fixedly coupled to the insert 800. There is no biased plunger in the insert rather a bore 806 extends from the first end 802 to the second end 804.

Figure 8C:
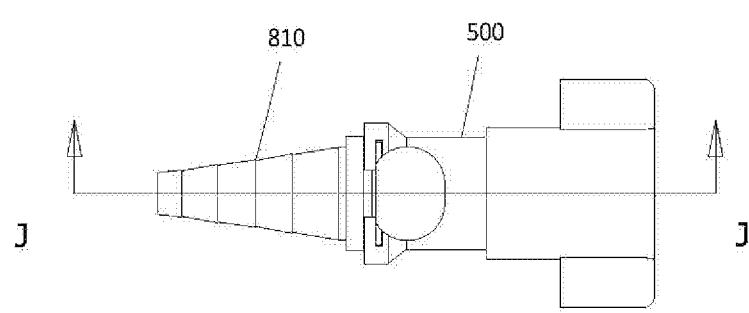
FIG. 8C illustrates an assembled or connected view of the oxygen quick-connect shut off body assembly and the adapter insert according to another embodiment of the invention.
Figure 8D:
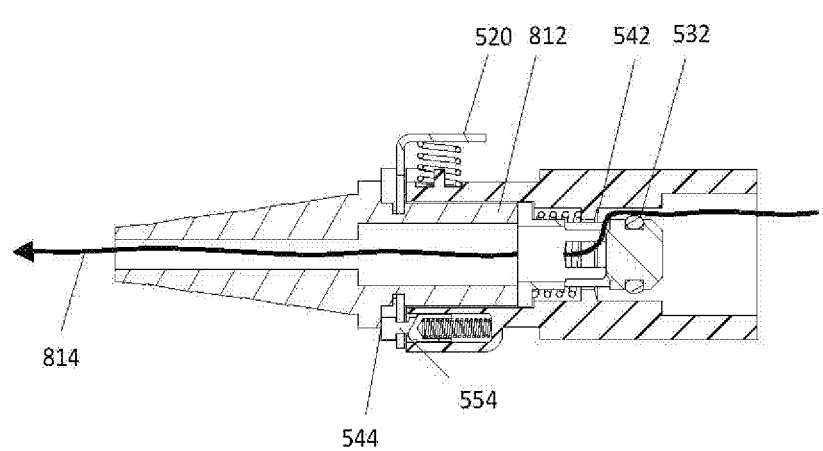
FIG. 8D illustrates a cross-sectional view of FIG. 8C along line J to J.

FIG. 8C illustrates an assembled or connected view of the oxygen quick-connect shut off body assembly and the adapter insert according to another embodiment of the invention. FIG. 8D illustrates a cross-sectional view of FIG. 8C along line J to J.

Referring to FIGS. 8C-8D, illustrate a quick-connect device 500 is connected to an insert 800. The first end 802 of the male insert 800 is inserted into the first end 504 of the female shut off body 500. The second end of the 506 may be connected to an oxygen gas source (e.g., a standard hospital-room oxygen line output, regulator) through connection mechanism 511 (not shown).

In operation, the first end 802 is inserted into the first end 504 until the catch device 512 engages the groove 808 in the male insert 800. There is an audible "click" to signal that a proper connection has been established by the recess portion 554 of the catch pin 544 engaging the with the catch plate 512 at releasably coupling to the third section 526. Optionally, one or more sensors is arranged in either the quick connect assembly 500 or the insert 800 configured to measure one or more of temperature, flowrate, location, unique product ID, unique patient ID or the information. The sensor is optionally configured with a network interface to provide communication to external device. There is no biased plunger in the insert rather a bore extends from the first end to the second end.

The end portion 812 of the insert 800 engages the inner bore 508 of the female coupling 500 to form a seal. In this embodiment, gas is being used as the fluid and a perfect seal is not required. It is believed there is no or substantially no leaking for gas when the two devices are coupled. Upon coupling, the biased plunger 528 in the female coupling 502 engages an end of the insert 800, thereby moving the biased plunger 528 in the shut off body 500 from a closed position to an open position. The catch pin 544 recess 554 is engaged with a portion 526 of the catch plate 514 releasably locking the insert 800 to the quick connect assembly 500 and allowing the plunger to move to an open position. In the open position seal member 532 not directly adjacent to the seat 542 of the inner bore 508 to allow gas to flow as indicated by arrow 814. That is, unseating seal member 532 from the seal 542 allows gas or fluid communication through the quick-connect device 500 as indicated by the arrow 814. That is, oxygen flows from the oxygen source (not shown), into the female coupling 500, through at least a portion of the plurality of windows 533 through the hollow end 536 of the plunger 528 and into the first end 802 of the male insert 800 and through the bore 806 and out the second end 804 to a secondary device (not shown) that can be attached. Optionally, the secondary device can be an oxygen delivery device can be a nasal cannula or a humidifier.

To uncouple or disconnect the insert 800 from the shut off body 500, the catch device 512 is depressed via the tab 520 to disengage the catch device 512 from the groove 808 in the male insert 800 and disengage the catch pin 544 from the catch device. When disengaged, the biased plunger 528 and seal member 532 is re-seated on the seat 542 to prevent oxygen flow through the quick-connect device 500.

Figure 9A:
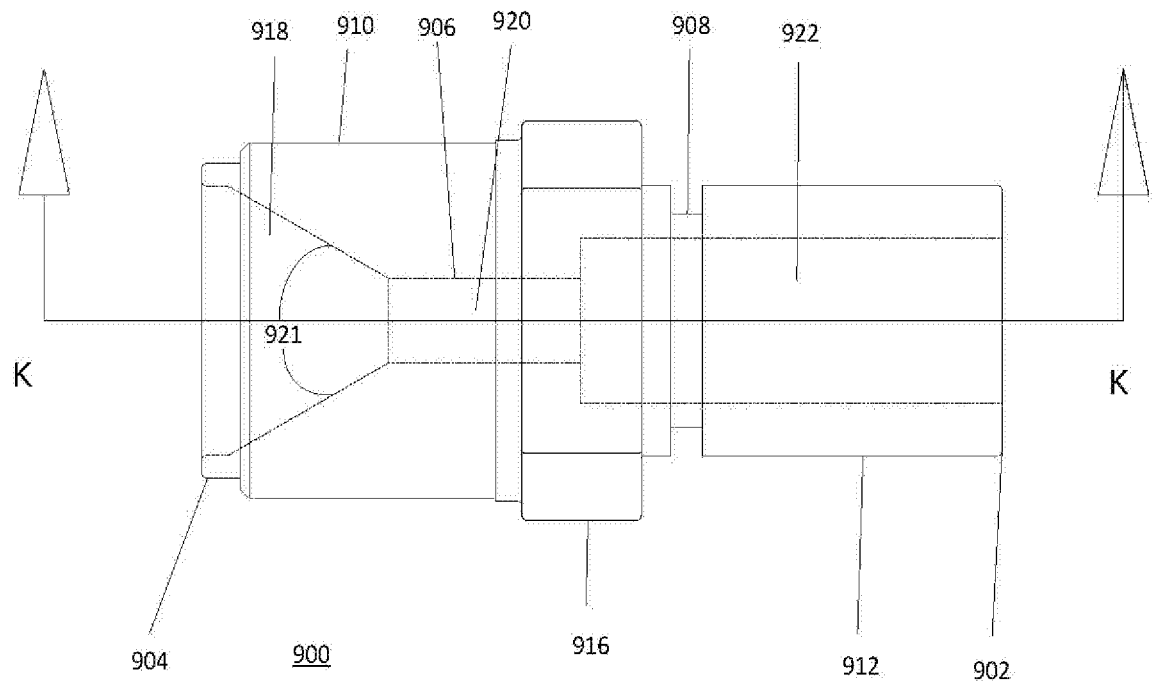
FIG. 9A illustrates a side view of a humidifier adapter insert according to another embodiment of the invention.
Figure 9B:
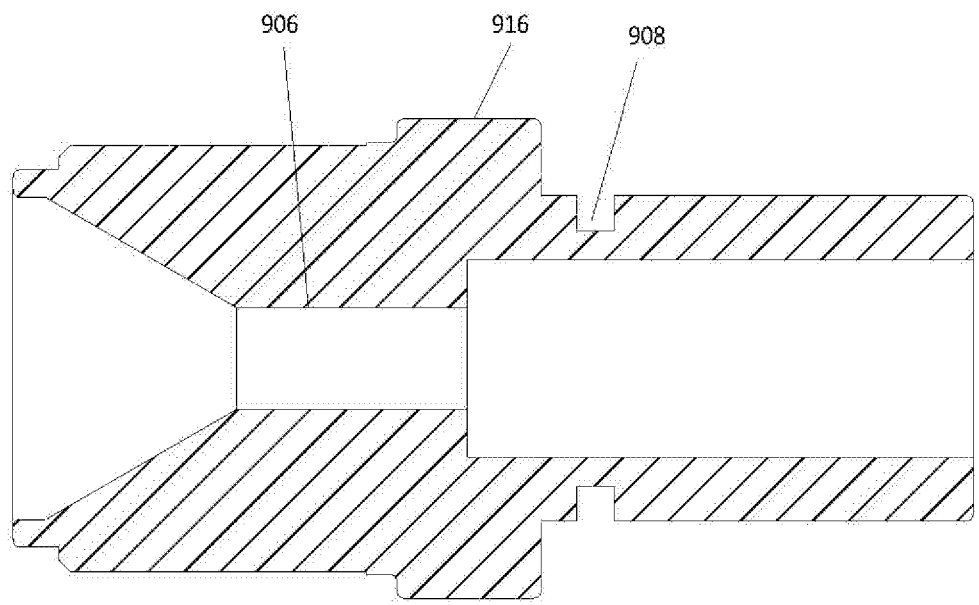
FIG. 9B illustrates a cross-sectional view of FIG. 9A along line K to K.

FIG. 9A illustrates a side view of a humidifier adapter insert according to another embodiment of the invention. FIG. 9B illustrates a cross-sectional view of FIG. 9A along line K to K.

Referring to FIGS. 9A-9B, a humidifier adapter 900 includes a first end 902, a second end 904 and a bore 906 or opening extending longitudinally through the first end 902 and to the second end 904. The humidifier adapter 900 is configured to be coupled to a humidifier for all the benefits described herein. The insert 900 includes a circumferential groove 908 disposed on the insert 900, which the catch device 512 of the shut off body 500 engages when the shut off body 500 is assembled with the insert 900. The insert 900 does not include a seal member, e.g., O-ring. The second end 904 of the male insert 910 includes a connection mechanism 910, e.g., threads, on the outer surface and is configured to be connected to a humidifier container. The bore of 906 of the insert 900 extends from the first end 902 to the second end 904. The bore includes a first section 918 extending into a second section 920 and the second section 920 extending into the third section 922. The first section 918 includes a conical configuration at a about a 60 degree wedge 921. The conical configuration of the first section 918 is configured to maximize air flow and seat and seal on the humidifier (not shown) by substantially matching the inlet conical configuration geometry of the humidifier. There is no biased plunger in the insert rather a bore 906 extends from the first end 902 to the second end 904. A protrusion 916 is configured to receive a tool to assist with rotation of the insert 900.

Figure 9C:
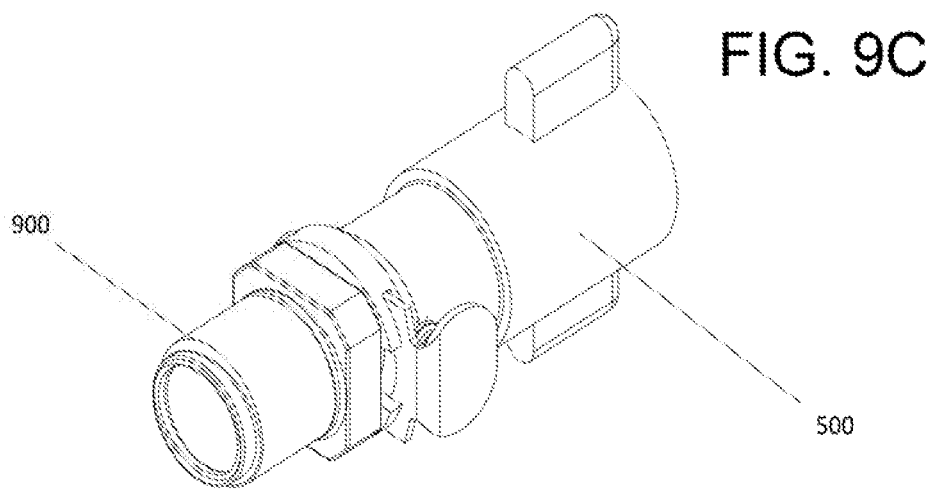
FIG. 9C illustrates perspective view of an assembled or connected view of the oxygen quick-connect shut off body assembly and the humidifier adapter insert according to another embodiment of the invention.
Figure 9D:
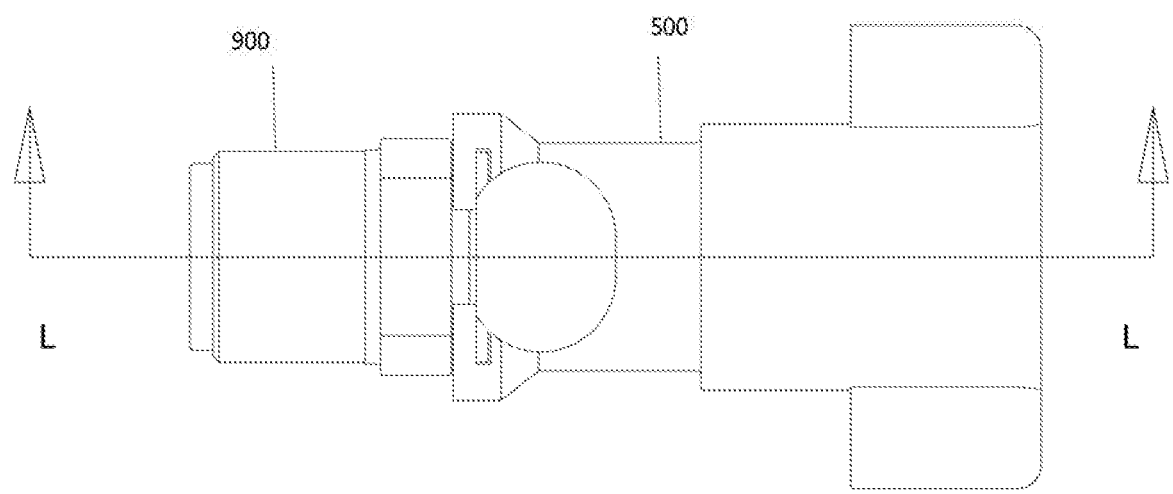
FIG. 9D illustrates top view of FIG. 9C.

FIG. 9C illustrates perspective view of an assembled or connected view of the oxygen quick-connect shut off body assembly and the humidifier adapter insert according to another embodiment of the invention. FIG. 9D illustrates top view of FIG. 9C.

Figure 9E:
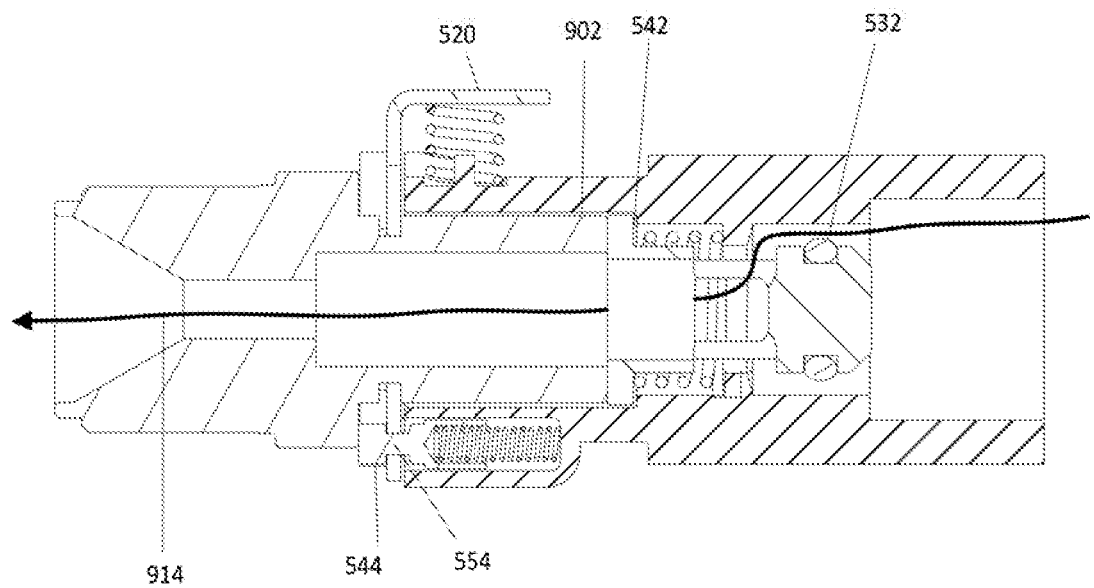
FIG. 9E illustrates a cross-sectional view of FIG. 9D along line L to L.

FIG. 9E illustrates a cross-sectional view of FIG. 9D along line L to L.

Referring to FIGS. 9C-9E, illustrate a quick-connect device 500 is connected to the insert 900. The first end 902 of the male insert 900 is inserted into the first end 504 of the female shut off body 500. The second end 506 of the quick connect device 500 may be connected to an oxygen gas source (e.g., a standard hospital-room oxygen line output, regulator) through connection mechanism 511 (not shown). The second end 904 of the insert 900 is connected to a humidifier configured to provide humidity to the oxygen (not shown).

In operation, the first end 902 is inserted into the first end 504 until the catch device 512 engages the groove 908 in the male insert 900. There is an audible "click" to signal that a proper connection has been established by the recess portion 554 of the catch pin 544 engaging the with the catch plate 512 at releasably coupling to the third section 526. Optionally, one or more sensors is arranged in either the quick connect assembly 500 or the insert 900 configured to measure one or more of temperature, moisture, flowrate, location, unique product ID, unique patient ID or the information. The sensor is optionally configured with a network interface to provide communication to external device. There is no biased plunger in the insert rather a bore extends from the first end to the second end.

The end portion 912 of the insert 900 engages the inner bore 508 of the female coupling 500 to form a seal. In this embodiment, gas is being used as the fluid and a perfect seal is not required. It is believed there is no or substantially no leaking for gas when the two devices are coupled. Upon coupling, the biased plunger 528 in the female coupling 500 engages an end of the insert 900, thereby moving the biased plunger 528 in the shut off body 500 from a closed position to an open position. The catch pin 544 recess 554 is engaged with a portion 526 of the catch plate 512 releasably locking the insert 900 to the quick connect assembly 500 and allowing the plunger to move to an open position. In the open position seal member 532 not directly adjacent to the seat 542 of the inner bore 508 to allow gas to flow as indicated by arrow 914. That is, unseating seal member 532 from the seal edge 542 allows gas or fluid communication through the quick-connect device 500 as indicated by the arrow 914. That is, oxygen flows from the oxygen source (not shown), into the female coupling 500, through at least a portion of the plurality of windows 533 through the hollow end 536 of the plunger 528 and into the first end 902 of the male insert 900 and through the bore 906 and out the second end 904 to a secondary device (not shown) that can be attached. Optionally, the secondary device can be an oxygen delivery device can be a nasal cannula or a humidifier.

To uncouple or disconnect the insert 800 from the shut off body 500, the catch device 512 is depressed via the tab 520 to disengage the catch device 512 from the groove 808 in the male insert 900 and disengage the catch pin 544 from the catch device. When disengaged, the biased plunger 528 and seal member 532 is re-seated on the seat 542 to prevent oxygen flow through the quick-connect device 500.

Figure 10A:
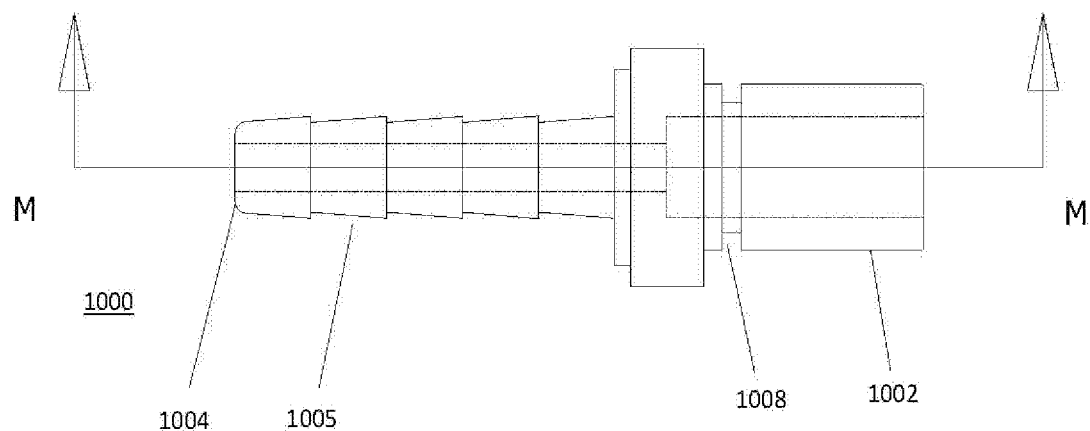
FIG. 10A illustrates a side view of a cannula adapter insert according to another embodiment of the invention.
Figure 10B:
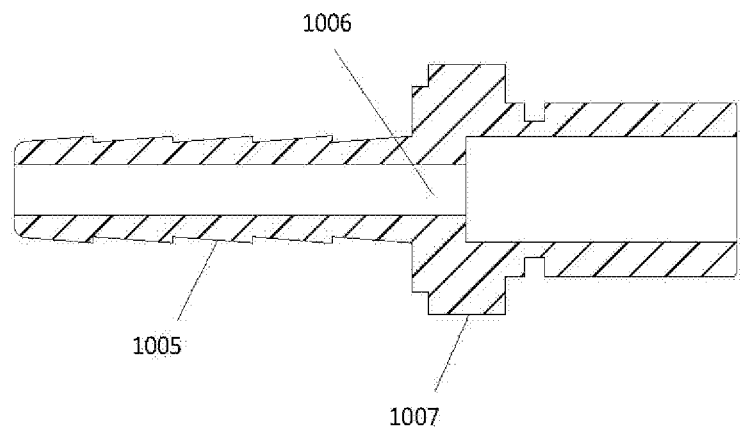
FIG. 10B illustrates a cross-sectional view of FIG. 10A along line M to M.

FIG. 10A illustrates a side view of a cannula adapter insert according to another embodiment of the invention. FIG. 10B illustrates a cross-sectional view of FIG. 10A along line M to M.

Referring to FIGS. 10A-10B, a cannula connection fitting 1000 having a first end 1002 and second end 1004 and a first bore 1006 or opening extending longitudinally through the first end 1002 and to the second end 1004. The cannula connection 1000 is configured to work with a conventional nasal cannula. In this embodiment, the first end 1002 includes a circumferential groove 1008 disposed on the insert 1000, which the catch device 512 of the shut off body 500 engages when the shut off body 500 is assembled with the insert 1000. The insert 1000 does not include a seal member, e.g., O-ring.

The second end 1004 of the male insert 1000 includes a Christmas tree connector 1005 that extends perpendicularly from the male insert body 1007. The Christmas tree connector 1005 includes deep grooved barbs over which the oxygen tubing slides in a first direction towards a protrusion 1007, but is configured to not move in a second opposite direction. The Christmas tree connector may be sized accordingly. The tapered configuration has a plurality staggered or grooved barbs over which the tubing slides in a first direction, but not in an opposite direction, and can become fixedly coupled to the insert 1000. There is no biased plunger in the insert rather a bore 1006 extends from the first end 1002 to the second end 1004.

Figure 10C:
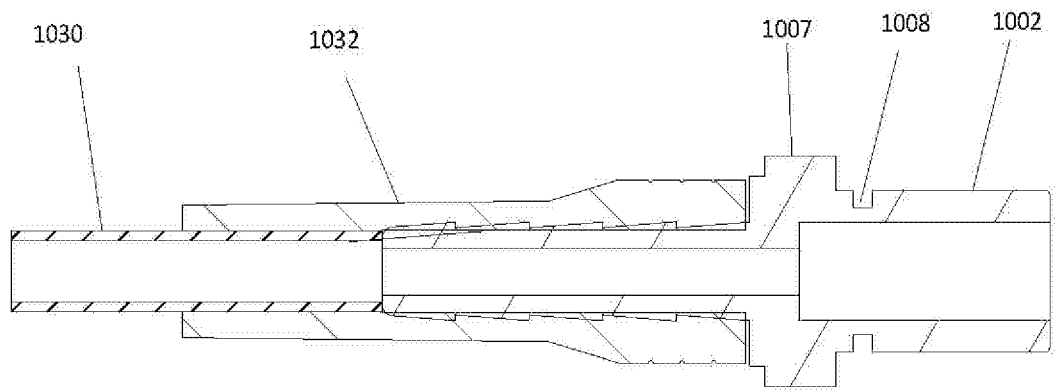
FIG. 10C cross-sectional view of FIG. 10D along line N to N.
Figure 10D:
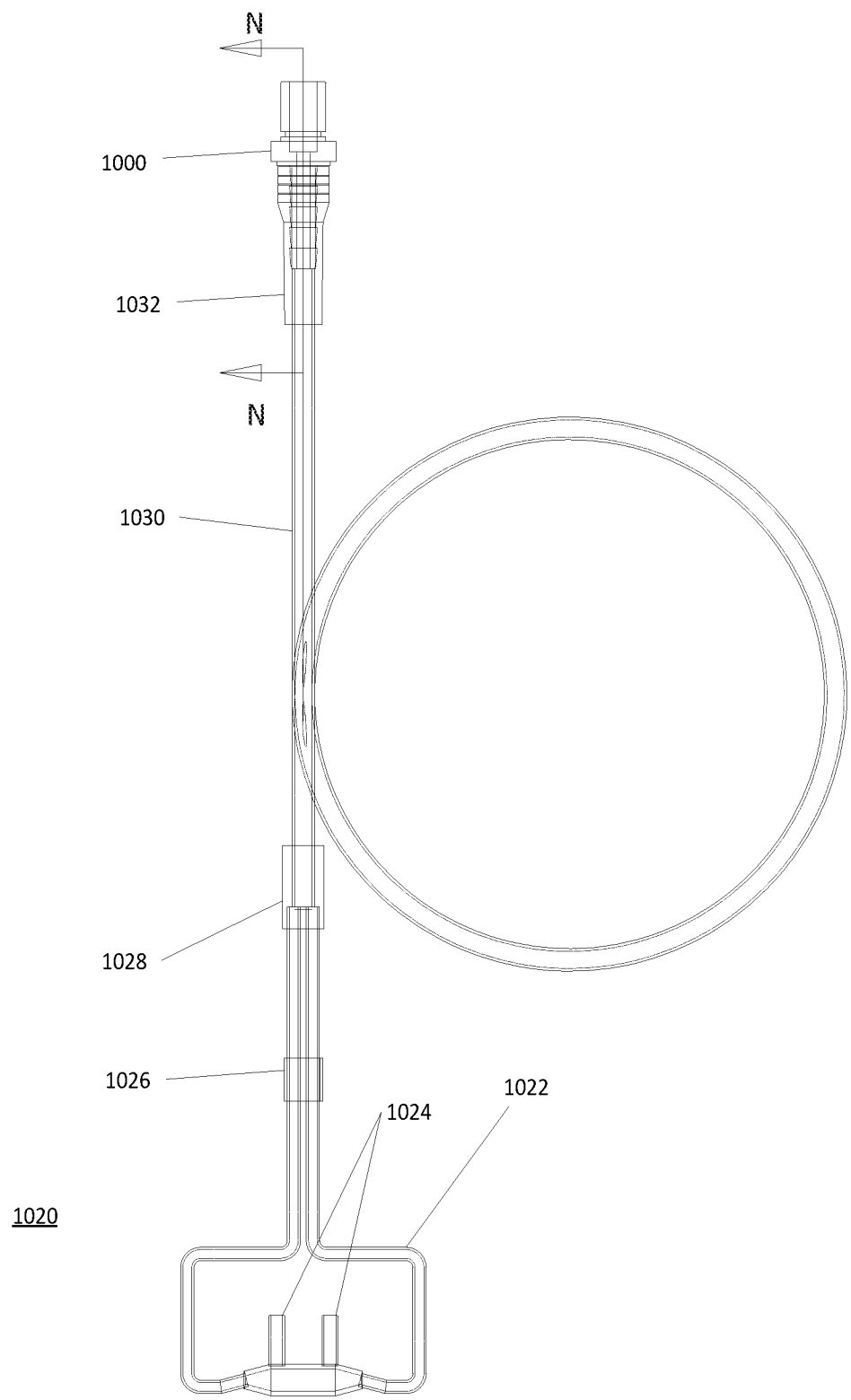
FIG. 10D illustrates a oxygen nasal cannula according to an embodiment of the invention.

FIG. 10C cross-sectional view of FIG. 10D along line N to N. FIG. 10D illustrates a oxygen nasal cannula according to an embodiment of the invention.

Referring to FIGS. 10C-10D, an extension tubing 1030 is coupled to a connection fitting 1032, the connection fitting 1032 is configured to engage the staggered or grooved barbs of the adapter 1000 to provide a coupled end. The connection fitting 1032 may be a press-fit connection with or without adhesive. Optionally, the connection fitting 1032 is not required and the extension tubing can be sized to fit over the second end 1004 and engage with barbs to fixedly couple the extension tubing to the adapter 1000.

Referring to FIG. 10D, the nasal cannula 1020 is a single disposable unit for use with our shut off body 500. The nasal cannula 1020 includes the adapter 1000 coupled to an extension tubing 1030 having a wye connector 1028, a slide bolo or adjuster 1026, headset loop 1022 and nasal prongs 1024.

The present disclosure, in various aspects, embodiments, and/or configurations, includes components, methods, processes, systems and/or apparatus substantially as depicted and described herein, including various aspects, embodiments, configurations embodiments, sub combinations, and/or subsets thereof. Those of skill in the art will understand how to make and use the disclosed aspects, embodiments, and/or configurations after understanding the present disclosure. The present disclosure, in various aspects, embodiments, and/or configurations, includes providing devices and processes in the absence of items not depicted and/or described herein or in various aspects, embodiments, and/or configurations hereof, including in the absence of such items as may have been used in previous devices or processes, e.g., for improving performance, achieving ease and/or reducing cost of implementation.

The foregoing discussion has been presented for purposes of illustration and description. The foregoing is not intended to limit the disclosure to the form or forms disclosed herein. In the foregoing description for example, various features of the disclosure are grouped together in one or more aspects, embodiments, and/or configurations for the purpose of streamlining the disclosure. The features of the aspects, embodiments, and/or configurations of the disclosure may be combined in alternate aspects, embodiments, and/or configurations other than those discussed above. This method of disclosure is not to be interpreted as reflecting an intention that the claims require more features than are expressly recited in each claim. Rather, as the following claims reflect, inventive aspects lie in less than all features of a single foregoing disclosed aspect, embodiment, and/or configuration. Thus, the following claims are hereby incorporated into this description, with each claim standing on its own as a separate preferred embodiment of the disclosure.

Moreover, though the description has included a description of one or more aspects, embodiments, and/or configurations and certain variations and modifications, other variations, combinations, and modifications are within the scope of the disclosure, e.g., as may be within the skill and knowledge of those in the art, after understanding the present disclosure. It is intended to obtain rights which include alternative aspects, embodiments, and/or configurations to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter.

What is claimed is:

1. A method of using an assembly for use with an oxygen gas supply source, comprising the steps of:
    obtaining a coupling body comprising a cylindrical main body having a first end, a second end and a longitudinal bore extending from the first end to the second end, wherein the first end comprises a catch plate configured to accept an insert assembly and the second end comprises an attachment mechanism;
    connecting the second end to the oxygen gas supply source;
    obtaining the insert assembly comprising a body having a first end, a second end and a longitudinal bore extending from the first end to the second end, a circumferential groove is arranged proximal to the first end and is configured to engage the catch plate and the insert assembly does not include a seal member; and
    arranging the first end of the insert assembly into the first end of the coupling body and engaging the catch plate with the circumferential grove to releasably couple the insert assembly to the coupling body.

2. The method of claim 1, wherein the insert assembly comprises a humidifier insert assembly, and
    wherein the bore on the second end of the insert assembly comprises a conical shape.

3. The method of claim 2, wherein the conical shape comprises an angle of about 150 degrees.

4. The method of claim 1, wherein the oxygen supply source comprises an oxygen flowrate device configured to permit adjustment of an oxygen flow rate.

5. The method of claim 4, further comprising the step of adjusting the oxygen flow rate to a predetermined flowrate greater than zero prior to the arranging the first end of the insert assembly into the first end of the coupling body.

6. The method of claim 1, further comprising the step of disconnecting the insert assembly from the coupling body.

7. The method of claim 5, disconnecting the insert assembly from the coupling body and after the disconnection of the insert assembly the oxygen gas is prevented from exiting the second end of the coupling.

8. The method of claim 7, further comprising the step of reconnecting the insert assembly by arranging the first end of the insert assembly into the first end of the coupling body and engaging the catch plate with the circumferential groove to releasably couple the insert assembly with the catch plate and the oxygen flow rate returns to the predetermined flowrate automatically without adjustment.

9. A method of using an assembly for use with an oxygen gas supply source, comprising the steps of:
    obtaining a coupling body comprising a cylindrical main body having a first end, a second end, and a longitudinal bore extending from the first end to the second end, and one or more sensors,
    wherein the first end comprises a catch plate configured to accept an insert assembly and the second end comprises an attachment mechanism;
    connecting the second end to the oxygen gas supply source;
    obtaining the insert assembly comprising a body having a first end, a second end and a longitudinal bore extending from the first end to the second end, and a circumferential groove arranged proximal to the first end configured to engage the catch plate, wherein the insert assembly does not include a seal member; and
    arranging the first end of the insert assembly into the first end of the coupling body and engaging the catch plate with the circumferential groove to releasably couple the insert assembly to the coupling body.

10. The method of claim 9, wherein the insert assembly comprises a nasal cannula adapter.

11. The method of claim 10, wherein the second end of the nasal cannula adapter comprises a tapered configuration and configured to be coupled to an extension tubing of a nasal cannula.

12. The method of claim 9, wherein the oxygen supply source comprises an oxygen flowrate device configured to permit adjustment of an oxygen flow rate, and
    further comprising the step of adjusting the oxygen flow rate to a predetermined flowrate greater than zero prior to the arranging the first end of the insert assembly into the first end of the coupling body.

13. The method of claim 12, further comprising the step of disconnecting the insert assembly from the coupling body without adjusting the oxygen flowrate.

14. The method of claim 13, wherein after the disconnection of the insert assembly from the coupling body step the oxygen gas is prevented from exiting the second end of the coupling body.

15. The method of claim 9, wherein the one or more sensors is configured to indicate one or more of temperature, flowrate, and other information.

16. The method of claim 9, wherein the one or more sensors comprises a radio frequency identification device (RFID).

17. A method of using a quick-connect assembly for use with an oxygen gas supply source, comprising the steps of:
   obtaining a coupling body comprising a cylindrical main body having a first end, a second end, and a longitudinal bore extending from the first end to the second end,
   wherein the first end comprises a catch plate configured to accept at least a portion of an insert assembly and the second end comprises an attachment mechanism, and a biased plunger arranged within the longitudinal bore of the cylindrical main body configured to move from a closed position to an open position,
   wherein the closed position prevents oxygen gas flow from the oxygen gas supply source from the second end to the first end, and wherein the open position permits oxygen gas flow from the oxygen gas supply source from the second end to the first end when the oxygen gas supply source is on and the second end is connected to the oxygen gas supply source;
   connecting the attachment mechanism of the coupling body to the oxygen gas supply source;
   obtaining the insert assembly comprising a body having a first end, a second end having a taper configurated that is configured to be connected to an oxygen tubing and a longitudinal bore extending from the first end to the second end, a circumferential groove is arranged proximal to the first end and is configured to engage the catch plate, and the insert assembly does not include a biased plunger or a seal member; and
   arranging the first end of the insert assembly into the first end of the coupling body and engaging a portion of the catch plate with the circumferential groove to releasably couple the insert assembly to the coupling body.

18. The method of claim 17, wherein the coupling body further comprises one or more sensors configured to wirelessly communicate with a secondary device upon a predetermined event.

19. The method of claim 18, wherein the predetermined event is programmable.

* * * * *

UNITED STATES PATENT AND TRADEMARK OFFICE
CERTIFICATE OF CORRECTION

PATENT NO. : 10,718,454 B2  
APPLICATION NO. : 15/498993  
DATED : July 21, 2020  
INVENTOR(S) : Aaron Decker Page 1 of 1

It is certified that error appears in the above-identified patent and that said Letters Patent is hereby corrected as shown below:

In the Claims

Claim 1, Column 17, Line 66, replace "grove" with -- groove --

Claim 7, Column 18, Line 19, replace "coupling" with -- coupling body --

Signed and Sealed this  
Twentieth Day of October, 2020

Andrei Iancu  
*Director of the United States Patent and Trademark Office*